(12) United States Patent
Higeta et al.

(10) Patent No.: US 8,232,375 B2
(45) Date of Patent: Jul. 31, 2012

(54) AZO COMPOUND, AND DYE-CONTAINING POLARIZING FILM COMPRISING THE SAME

(75) Inventors: Takahiro Higeta, Tokyo (JP); Hiroaki Ohno, Tokyo (JP); Yuichi Sadamitsu, Tokyo (JP)

(73) Assignees: Nippon Kayaku Kabushiki Kaisha, Tokyo (JP); Polatechno Co., Ltd., Niigata (JP)

( * ) Notice: Subject to any disclaimer, the term of this patent is extended or adjusted under 35 U.S.C. 154(b) by 348 days.

(21) Appl. No.: 12/739,210

(22) PCT Filed: Oct. 30, 2008

(86) PCT No.: PCT/JP2008/069723
§ 371 (c)(1),
(2), (4) Date: Apr. 22, 2010

(87) PCT Pub. No.: WO2009/057676
PCT Pub. Date: May 7, 2009

(65) Prior Publication Data
US 2010/0226008 A1    Sep. 9, 2010

(30) Foreign Application Priority Data

Nov. 2, 2007 (JP) ................................. 2007-285939

(51) Int. Cl.
G02B 5/30 (2006.01)
C07C 245/10 (2006.01)
(52) U.S. Cl. .... 534/560; 534/714; 534/815; 359/491.01
(58) Field of Classification Search ............. 359/491.01; 534/560, 815, 714
See application file for complete search history.

(56) References Cited

U.S. PATENT DOCUMENTS

| | | | |
|---|---|---|---|
| 2,004,250 A | 6/1935 | Schindhelm et al. | |
| 2,270,451 A | 1/1942 | Keller | |
| 2,671,775 A | 3/1954 | Hanhart | |
| 2,817,659 A * | 12/1957 | Bossard et al. | 534/797 |
| 4,051,123 A | 9/1977 | Piller et al. | |
| 4,118,232 A | 10/1978 | Piller et al. | |
| 4,556,707 A * | 12/1985 | Henk | 534/635 |
| 4,954,133 A | 9/1990 | Oppliger | |
| 5,007,942 A | 4/1991 | Claussen et al. | |
| 5,272,259 A | 12/1993 | Claussen et al. | |
| 5,318,856 A | 6/1994 | Misawa et al. | |

(Continued)

FOREIGN PATENT DOCUMENTS

DE   1644179 B   7/1971

(Continued)

OTHER PUBLICATIONS

Final Rejection mailed Feb. 8, 2012 in co-pending U.S. Appl. No. 13/181,743.

(Continued)

Primary Examiner — Satya Sastri
(74) Attorney, Agent, or Firm — Nields, Lemack & Frame, LLC

(57) ABSTRACT

Disclosed is an azo compound represented by the formula (1) or (2) or a salt thereof. The azo compound or the salt thereof has an excellent light-polarizing property, and is extremely useful as a dichroic dye for use in a polarizing plate that shows less color leakage in a visible light range or a polarizing plate for a liquid crystal projector comprising the aforementioned polarizing plate. (1) (2) wherein $R_1$ represents a hydrogen atom, a lower alkyl group, a lower alkoxy group, a hydroxyl group, a sulfonate group or a carboxyl group; $R_2$ to $R_5$ independently represent a hydrogen atom, a lower alkyl group, a lower alkoxy group or an acetylamino group; X represents a benzoylamino group which may have a substituent, a phenylamino group which may have a substituent, a phenylazo group which may have a substituent, or a naphthotriazole group which may have a substituent; m represents a numeral number of 1 or 2; and n represents a numeral number of 0 or 1.

(1)

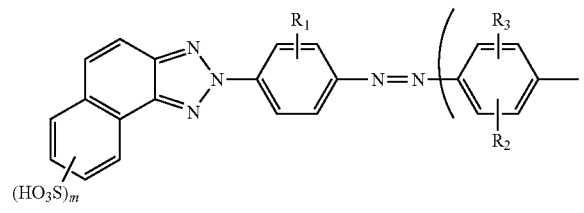

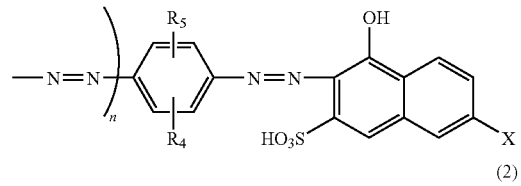

(2)

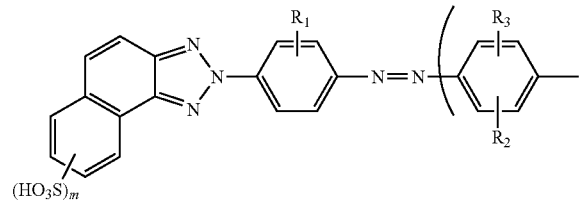

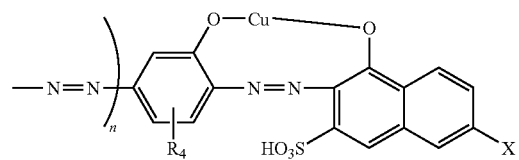

25 Claims, No Drawings

U.S. PATENT DOCUMENTS

| | | | |
|---|---|---|---|
| 5,446,135 | A | 8/1995 | Misawa et al. |
| 5,700,296 | A | 12/1997 | Ogino et al. |
| 5,731,421 | A | 3/1998 | Tzikas et al. |
| 5,739,298 | A | 4/1998 | Misawa et al. |
| 6,049,428 | A | 4/2000 | Khan et al. |
| 6,399,752 | B1 | 6/2002 | Ohta et al. |
| 6,563,640 | B1 | 5/2003 | Ignatov et al. |
| 6,699,976 | B2 | 3/2004 | Ashida et al. |
| 6,790,490 | B1 | 9/2004 | Oiso et al. |
| 7,245,431 | B2 | 7/2007 | Watson et al. |
| 7,304,147 | B2 | 12/2007 | Sadamitsu et al. |
| 7,387,668 | B2 | 6/2008 | Kitayama et al. |
| 7,445,822 | B2 | 11/2008 | Sadamitsu |
| 7,514,129 | B2 | 4/2009 | Sadamitsu |
| 7,931,702 | B2 | 4/2011 | Sadamitsu et al. |
| 2003/0098447 | A1 | 5/2003 | Ashida et al. |
| 2004/0232394 | A1* | 11/2004 | Khan et al. ............ 252/585 |
| 2005/0003109 | A1 | 1/2005 | Oiso et al. |
| 2007/0079740 | A1 | 4/2007 | Sadamitsu et al. |
| 2007/0119341 | A1 | 5/2007 | Kitayama et al. |
| 2007/0166483 | A1 | 7/2007 | Sadamitsu |
| 2008/0094549 | A1 | 4/2008 | Sadamitsu |
| 2010/0257678 | A1 | 10/2010 | Sadamitsu et al. |
| 2011/0060134 | A1 | 3/2011 | Sadamitsu et al. |
| 2011/0063546 | A1 | 3/2011 | Sadamitsu et al. |
| 2011/0075076 | A1 | 3/2011 | Nishiguchi et al. |
| 2011/0089383 | A1 | 4/2011 | Sadamitsu et al. |
| 2011/0164208 | A1 | 7/2011 | Nishiguchi et al. |
| 2011/0267691 | A1 | 11/2011 | Sadamitsu et al. |

FOREIGN PATENT DOCUMENTS

| | | | |
|---|---|---|---|
| DE | 3236238 | A1 | 5/1984 |
| EP | 0146747 | A2 | 7/1985 |
| EP | 0530106 | A1 | 3/1993 |
| EP | 0549342 | A2 | 6/1993 |
| EP | 0626598 | A2 | 11/1994 |
| EP | 0632105 | A1 | 1/1995 |
| EP | 0982371 | A1 | 3/2000 |
| EP | 1203969 | A1 | 5/2002 |
| FR | 1541972 | B | 10/1968 |
| GB | 954100 | B | 4/1964 |
| JP | 47-018548 | B1 | 5/1972 |
| JP | 58-145761 | A | 8/1983 |
| JP | 60-115671 | A | 6/1985 |
| JP | 60-156759 | A | 8/1985 |
| JP | 60-168743 | A | 9/1985 |
| JP | 60-243157 | A | 12/1985 |
| JP | 60-243176 | A | 12/1985 |
| JP | 2-269136 | A | 11/1990 |
| JP | 3-12606 | A | 1/1991 |
| JP | 5-295281 | A | 11/1993 |
| JP | 2622748 | B2 | 4/1997 |
| JP | 2001-33627 | A | 2/2001 |
| JP | 2001-56412 | A | 2/2001 |
| JP | 2001-108828 | A | 4/2001 |
| JP | 2001-240762 | A | 9/2001 |
| JP | 2002-275381 | A | 9/2002 |
| JP | 2003-35819 | A | 7/2003 |
| JP | 2003-215338 | A | 7/2003 |
| JP | 2004-51645 | A | 2/2004 |
| JP | 2004-75719 | A | 3/2004 |
| JP | 2004-323712 | A | 11/2004 |
| JP | 2004-338876 | A | 12/2004 |
| RU | 2110822 | C1 | 5/1998 |
| RU | 2155978 | C2 | 9/2000 |
| WO | 2004/013232 | A1 | 2/2004 |
| WO | 2004/092282 | A1 | 10/2004 |
| WO | 2005/033211 | A1 | 4/2005 |
| WO | 2005/075572 | A1 | 8/2005 |
| WO | 2006/057214 | A1 | 6/2006 |
| WO | 2007/145210 | A1 | 12/2007 |
| WO | 2007/148757 | A1 | 12/2007 |

OTHER PUBLICATIONS

Final Rejection mailed Feb. 9, 2012 in co-pending U.S. Appl. No. 12/227,994.
Senryo Kagaku (Dye Chemistry), with English Translations, 1st Edition Nov. 30, 1957, 4th Edition Aug. 15, 1966, pp. 611-613.
Senryo Kagaku (Dye Chemistry), with English Translations, 1st Edition Nov. 30, 1957, 4th Edition Aug. 15, 1966, p. 626.
Thieme, vol. 10/3, Part 3 (1952), pp. 339-346, XP 002536512, "Methoden der Organischen Chemie", Houben, et al.
J. Chem. Soc. Pak., vol. 24, No. 1, (2002), pp. 10-17, "Stilbene Based Direct Effect of Fixing Agents on the Fastness and Colour Properties", Waheed, et al.
International Search Report dated Jun. 26, 2007 in co-pending foreign application No. PCT/JP2007/060623.
European Communication dated Oct. 12, 2009 in co-pending foreign application No. PCT/JP2007/060623.
Russian Communication dated Feb. 12, 2011 in co-pending foreign application No. RU 2008152360/05.
European Communication dated Jul. 28, 2009 in co-pending foreign application PCT/JP2007/061813.
International Search Report dated Sep. 11, 2007 in co-pending foreign application PCT/JP2007/061813.
European Communication dated Jul. 28, 2009 in co-pending foreign application PCT/JP2007/062509.
European Communication dated May 7, 2010 in co-pending foreign application EP 10151418.0.
Russian Communication dated Nov. 3, 2010 in co-pending foreign application RU 2009101945/05.
Intenational Search Report dated Sep. 11, 2007 in co-pending foreign application PCT/JP2007/062509.
International Search Report dated Aug. 4, 2009 in co-pending foreign application PCT/JP2009/059173.
International Search Report dated Aug. 4, 2009 in co-pending foreign application PCT/JP2009/059172.
Office Action dated Nov. 4, 2010 in co-pending U.S. Appl. No. 12/227,613.
Notice of Allowance dated Dec. 15, 2010 in co-pending U.S. Appl. No. 12/227,613.
Office Action dated Sep. 30, 2010 in co-pending U.S. Appl. No. 12/308,282.
Final Rejection dated Mar. 17, 2011 in co-pending U.S. Appl. No. 12/308,282.
Japanese Communication with English translation, issued Apr. 27, 2012 and mailed May 8, 2012, in co-pending Japanese Patent Application No. JP 2008-517886.
Senryo Kagaku (Dye Chemistry), by Yutaka Hosoda; pp. 618-619 and pp. 634-635, with English translations; 4th Edition; Aug. 15, 1966.
International Search Report dated Dec. 9, 2008 in corresponding foreign application (PCT/JP2008/069723).
Office Action dated Aug. 11, 2011 in co-pending U.S. Appl. No. 12/227,994.
Office Action dated Aug. 12, 2011 in co-pending U.S. Appl. No. 13/181,743.
EPO Machine Translation of FR 1541972, Farbenfabriken Bayer; Colorants Disazoiques, Oct. 26, 1967.

* cited by examiner

AZO COMPOUND, AND DYE-CONTAINING POLARIZING FILM COMPRISING THE SAME

TECHNICAL FIELD

The present invention relates to a novel azo compound and a dye-containing polarizing film comprising the same.

BACKGROUND ART

A polarizing plate having a function to transmit or shield light is, along with liquid crystals which have a function of switching light, a fundamental constituent element of a display apparatus such as a liquid crystal display (LCD). The area of application of this LCD has expanded broadly from the early day small items such as an electronic calculator and a watch to a notebook computer, a word processor, a liquid crystal projector, a liquid crystal television, a car navigation system, and indoor and outdoor measurement instruments. Also, the LCD is used in broad conditions from low to high temperature, from low to high humidity, and from low to high light intensity. Thus, a polarizing plate having high polarization performance and excellent durability is desired.

At present, the polarizing film is produced by dyeing a polarizing film substrate with or incorporating therein iodine or a dichroic dye as a polarizing element, where the substrate is a stretched and oriented film of polyvinyl alcohol or its derivative, or an oriented film of polyene prepared by dehydrochlorination of a polyvinyl chloride film or dehydration of a polyvinyl alcohol film. Among these, an iodine polarizing film which uses iodine as the polarizing element exhibits superior polarization performance. However, this polarizing film is weak to moisture and heat, and when it is used for a long time under conditions of high temperature and high humidity, a problem of durability arises. In order to improve durability, methods such as treating the polarizing film with formalin or an aqueous solution containing boric acid and using a polymer film of low moisture permeability as a protective film are considered. However, the effects of these methods are not satisfactory. On the other hand, a dye-containing polarizing film comprising a dichroic dye as the polarizing element has better moisture resistance and heat resistance than the iodine polarizing film, but, generally, is insufficient in polarization performance.

In a neutral color polarizing film produced by adsorbing several kinds of dichroic dyes to a polymer film followed by orientation, if there is light leakage (color leakage) of a specific wavelength in the wavelength range of visible light, in a state (the perpendicular position) where two polarizing films are superimposed on each other in such a way that their orientation directions are perpendicular to each other, the hues of the liquid crystal display may change in the dark state when the polarizing films are fixed to the liquid crystal display panel. Thus, in order to prevent the discoloration of the liquid crystal display due to color leakage of a specific wavelength in the dark state when the polarizing film is fixed to a liquid crystal display apparatus, it is necessary to uniformly lower the transmittance at the perpendicular position (perpendicular transmittance) in the wavelength range of visible light.

Further, in a case of a color liquid crystal projection type display, namely, a color liquid crystal projector, a polarizing plate is used for the liquid crystal image-forming part. In this application, the iodine polarizing plate was used previously, which has good polarization performance and exhibits neutral gray color. However, as mentioned above, the iodine polarizing plate has a problem that its light resistance, heat resistance, and wet heat resistance are not sufficient, because iodine is the polarizer. In order to solve this problem, a neutral gray polarizing plate using a dye type dichroic colorant as the polarizer has come to be used. In the neutral gray polarizing plate, usually colorants of three primary colors are used in combination in order to improve transmittance in the entire wavelength range of visible light and polarization performance evenly. Thus, there is a problem that, to meet the demand of the marketplace for more brightness as in the color liquid crystal projector, the light transmittance is still poor and, in order to realize brightness, it is necessary to increase intensity of the light source. In order to solve this problem, three polarizing plates corresponding to the three primary colors, namely, plates for each of the blue channel, the green channel, and the red channel have come to be used.

However, decrease in brightness cannot be avoided because light is absorbed considerably by the polarizing plate and an image of such a small area as 0.5 to 3 inches is magnified to about several tens to one hundred and tens of inches. Therefore, as the light source, one of high luminance is used. Furthermore, desire for further increase in brightness of the liquid crystal projector is strong and, as a result, the intensity of the light source used is inevitably growing stronger. Along with this, the amounts of light and heat the polarizing plate receives are increasing.

A dye which may be used for producing the dye-containing polarizing film as mentioned above includes the water-soluble azo compounds described, for example, in Patent Documents 1 to 6.

However, conventional polarizing plates comprising the water-soluble dye have not yet satisfied the market needs sufficiently in terms of polarization characteristics, the range of absorption wavelength, hues, and the like. Furthermore, among three polarizing plates corresponding to the three primary colors for a color liquid crystal projector, namely, the plates for each of the blue channel, the green channel, and the red channel, none is good in all of brightness, polarization performance, durability under a condition of high temperature and high humidity, and resistance to prolonged irradiation of light. Thus, improvement is desired.

PATENT DOCUMENT 1: JP 2001-33627 A
PATENT DOCUMENT 2: JP 2001-56412 A
PATENT DOCUMENT 3: Japanese Patent No. 2622748
PATENT DOCUMENT 4: JP 2004-51645 A
PATENT DOCUMENT 5: WO 2004/092282
PATENT DOCUMENT 6: WO 2006/057214
NON-PATENT DOCUMENT 1: "Dyestuff Chemistry" by Yutaka Hosoda

DISCLOSURE OF THE INVENTION

Problems to be Solved by the Invention

An object of the present invention is to provide a polarizing plate of high performance having excellent polarization performance and resistance to moisture, heat, and light. Furthermore, another object of the present invention is to provide a polarizing plate of high performance which does not cause color leakage at the perpendicular position in the wavelength range of visible light and which has excellent polarization performance and resistance to moisture, heat, and light, the polarizing plate being a neutral color polarizing plate produced by adsorbing two or more kinds of dichroic dyes in a polymer film, followed by orientation thereof.

A further object of the present invention is to provide polarizing plates of high performance corresponding to the three primary colors for a color liquid crystal projector, which are good in all of brightness, polarization performance, durability, and light resistance.

Means for Solving the Problems

The present inventors conducted diligent research in order to accomplish these objects and, as a result, found that a polarizing film and a polarizing plate comprising a specific azo compound and/or a salt thereof show excellent polarization performance and resistance to moisture, heat, and light. This finding led to the present invention. Namely, the present invention provides the following:

(1) An azo compound represented by the following formula (1) or a salt thereof:

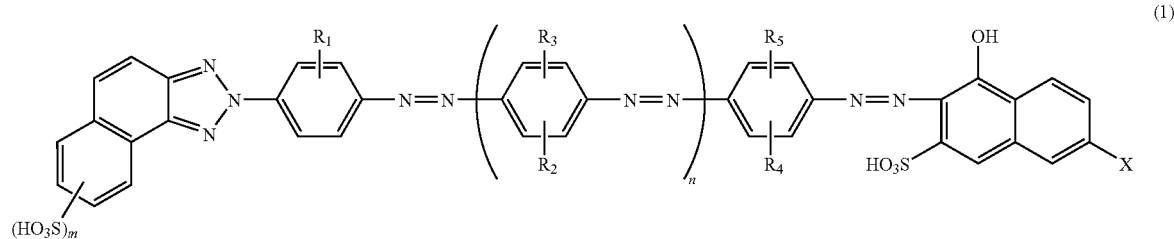

wherein $R_1$ represents a hydrogen atom, a lower alkyl group, a lower alkoxyl group, a hydroxyl group, a sulfonic acid group, or a carboxyl group; $R_2$ to $R_5$ each independently represent a hydrogen atom, a lower alkyl group, a lower alkoxyl group, or an acetylamino group; X represents a benzoylamino group which may have one or more substituents, a phenylamino group which may have one or more substituents, a phenylazo group which may have one or more substituents, or a naphthotriazole group which may have one or more substituents; m represents 1 or 2; and n represents 0 or 1.

(2) An azo compound represented by the following formula (2) or a salt thereof:

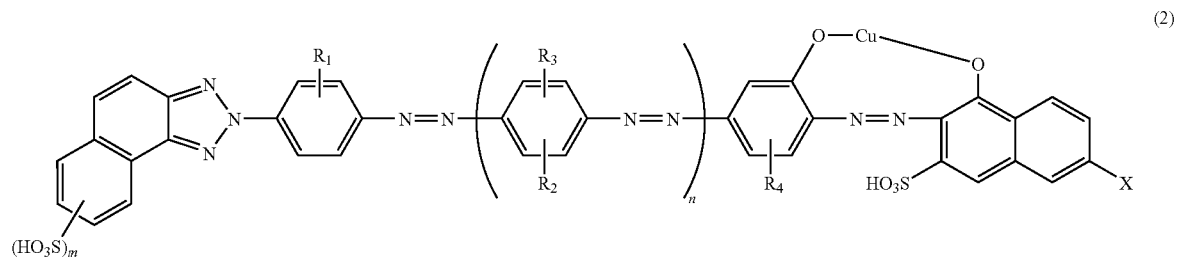

wherein $R_1$ to $R_4$, X, m, and n represent the same meanings as in the formula (1).

(3) The azo compound according to (1) or (2) above or a salt thereof, wherein X is a benzoylamino group which may have one or more substituents, a phenylamino group which may have one or more substituents, a phenylazo group which may have one or more substituents, or a naphthotriazole group which may have one or more substituents, wherein each of the one or more substituents is independently a hydrogen atom, a lower alkyl group, a lower alkoxyl group, a hydroxyl group, a carboxyl group, a sulfonic acid group, a nitro group, an amino group, or a substituted amino group.

(4) The azo compound according to (1) or (2) above or a salt thereof, wherein X is a naphthotriazole group represented by the following formula (3):

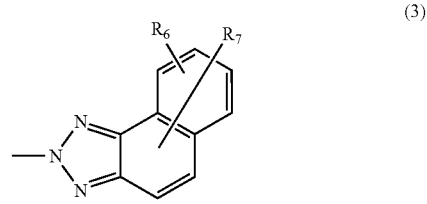

wherein $R_6$ and $R_7$ each independently represent either a hydrogen atom or a sulfonic acid group.

(5) The azo compound according to (1) or (2) above or a salt thereof, wherein X is a benzoylamino group represented by the following formula (4):

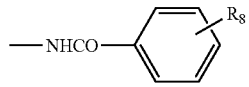

(4)

wherein $R_8$ represents any one of a hydrogen atom, an amino group, or a substituted amino group.

(6) The azo compound according to (1) or (2) above or a salt thereof, wherein X is a phenylamino group represented by the following formula (5):

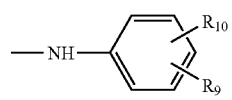

(5)

wherein $R_9$ and $R_{10}$ each independently represent any one of a hydrogen atom, a methyl group, a methoxy group, a sulfonic acid group, an amino group, or a substituted amino group.

(7) The azo compound according to (1) or (2) above or a salt thereof, wherein X is a phenylazo group represented by the following formula (6):

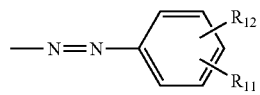

(6)

wherein $R_{11}$ and $R_{12}$ each independently represent any one of a hydrogen atom, a methyl group, a methoxy group, an amino group, a substituted amino group, or a hydroxyl group.

(8) The azo compound according to any one of (1) to (7) above or a salt thereof, wherein $R_1$ is a hydrogen atom, a methyl group, a hydroxyl group, a carboxyl group, or a sulfonic acid group.

(9) The azo compound according to any one of (1) to (8) above or a salt thereof, wherein each of $R_2$ to $R_5$ is independently a hydrogen atom, a methyl group, or a methoxy group.

(10) A dye-containing polarizing film, comprising an azo compound according to any one of (1) to (9) above and/or a salt thereof, contained in a polarizing film substrate.

(11) A dye-containing polarizing film, comprising an azo compound according to any one of (1) to (9) above and/or a salt thereof, and at least one kind of other organic dye, contained in the polarizing film substrate.

(12) A dye-containing polarizing film, comprising at least two kinds of azo compounds according to any one of (1) to (9) above and/or salts thereof, and at least one kind of other organic dye, contained in a polarizing film substrate.

(13) The dye-containing polarizing film according to any one of (10) to (12) above, wherein the polarizing film substrate is a film comprising a polyvinyl alcohol resin.

(14) A dye-containing polarizing plate, comprising a transparent protective layer adhered on at least one side of a dye-containing polarizing film according to any one of (10) to (12) above.

(15) A polarizing plate for a liquid crystal display, wherein a dye-containing polarizing film or a dye-containing polarizing plate according to any one of (10) to (14) above is used.

(16) A color polarizing plate for a liquid crystal projector, wherein a dye-containing polarizing film or a dye-containing polarizing plate according to any one of (10) to (14) above is used.

BEST MODE FOR CARRYING OUT THE INVENTION

The azo compound of the present invention is represented by the formula (1) or (2) mentioned above. In the formula (1) or (2), $R_1$ represents a hydrogen atom, a lower alkyl group, a lower alkoxyl group, a sulfonic acid group, a hydroxyl group, or a carboxyl group, of which a hydrogen atom, a methyl group, a sulfonic acid group, a hydroxyl group, or a carboxyl group is preferable; $R_2$ to $R_5$ each independently represent a hydrogen atom, a lower alkyl group, a lower alkoxyl group, or an acetylamino group, of which a hydrogen atom, a methyl group, or a methoxy group is preferable; X represents a benzoylamino group which may have one or more substituents, a phenylamino group which may have one or more substituents, a phenylazo group which may have one or more substituents, or a naphthotriazole group which may have one or more substituents, wherein each of the one or more substituents is preferably a hydrogen atom, a lower alkyl group, a lower alkoxyl group, a hydroxyl group, a carboxyl group, a sulfonic acid group, a nitro group, an amino group, or a substituted amino group; when X is the benzoylamino group which may have one or more substituents, each of the one or more substituents is preferably a hydrogen atom, an amino group, or a substituted amino group; when X is the phenylamino group which may have one or more substituents, each of the one or more substituents is preferably a hydrogen atom, a methyl group, a methoxy group, a sulfonic acid group, an amino group, or a substituted amino group; when X is the phenylazo group which may have one or more substituents, each of the one or more substituents is preferably a hydrogen atom, a methyl group, a methoxy group, an amino group, a substituted amino group, or a hydroxyl group; when X is the naphthotriazole group which may have one or more substituents, each of the one or more substituents is preferably a hydrogen atom or a sulfonic acid group; m represents 1 or 2, and n represents 0 or 1, where m is preferably 2 and n is preferably 0 or 1.

In the present invention, the substituted amino group is not particularly limited and includes, for example, an amino group substituted by a lower alkyl group or an acyl group. In addition, the lower alkyl group and the lower alkoxyl group refer, respectively, to a linear- or branched-chain alkyl group and alkoxyl group having 1 to 4 carbon atoms.

Next, specific examples of the azo compounds represented by the formula (1) or (2), to be used in the present invention, will be described below. Note that in the following formulae, the sulfonic acid group, the carboxylic group, and the hydroxyl group are shown in the form of free acids.

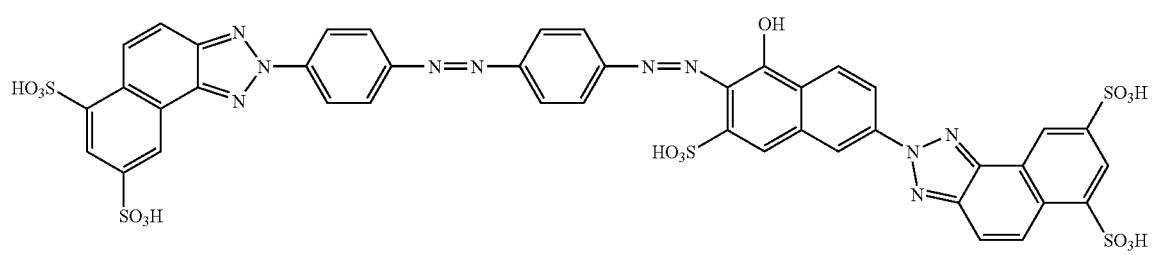
(7)
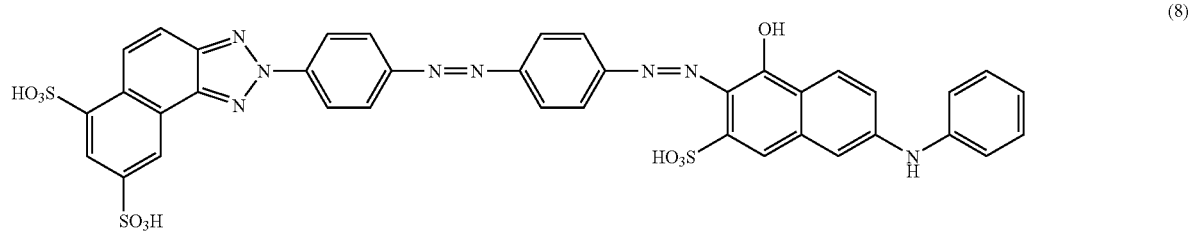
(8)
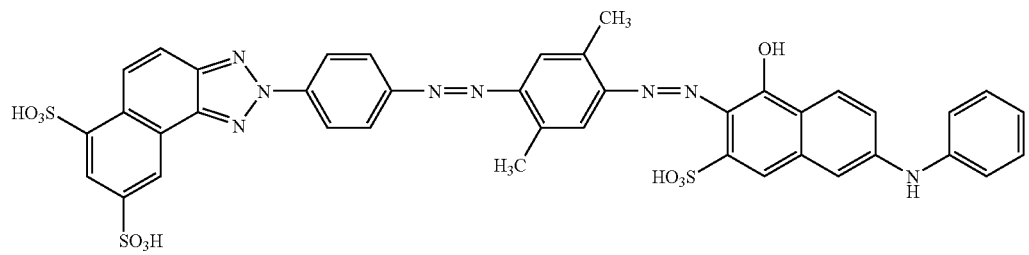
(9)
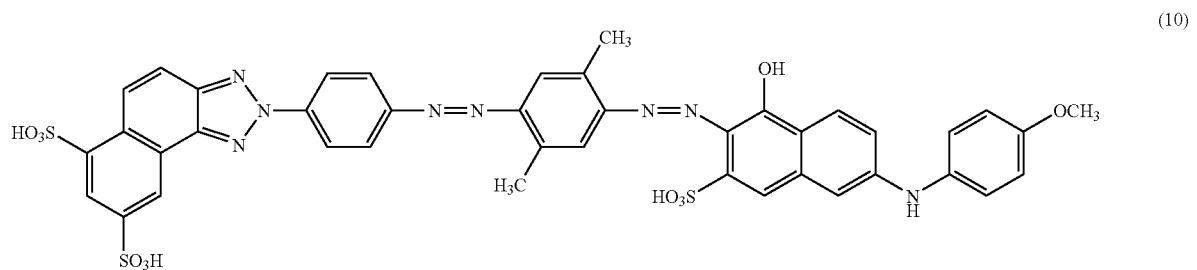
(10)
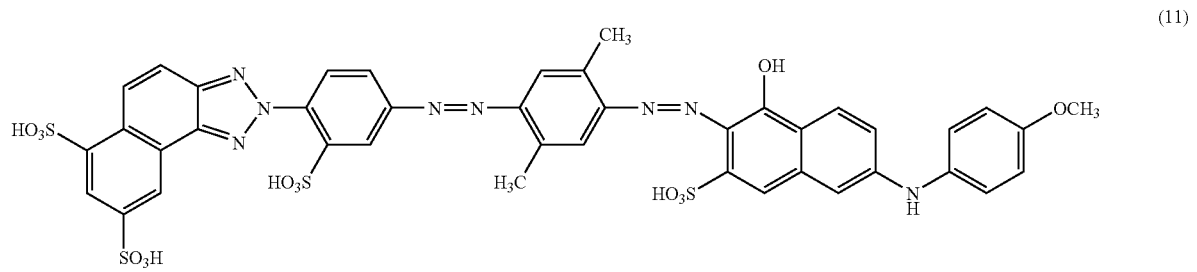
(11)
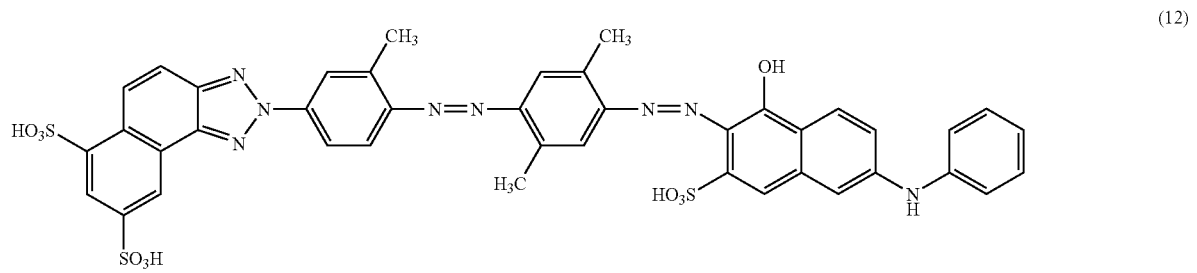
(12)

-continued
(13)
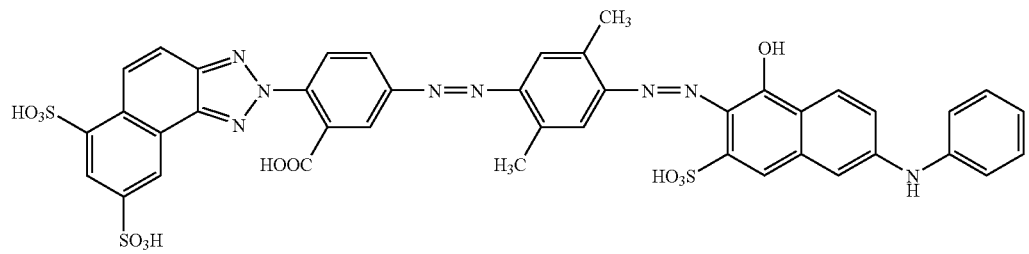
(14)
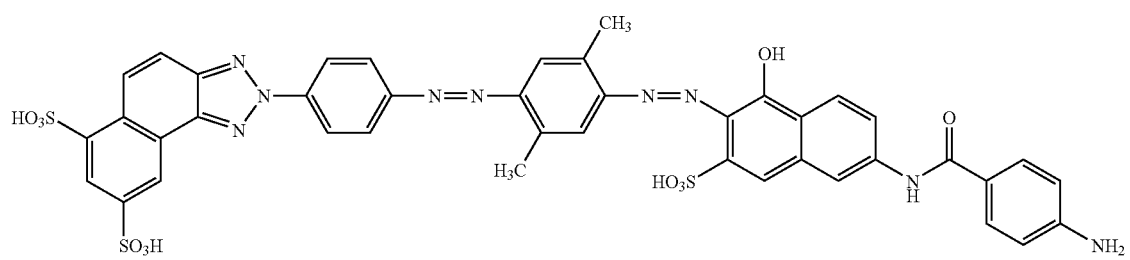
(15)
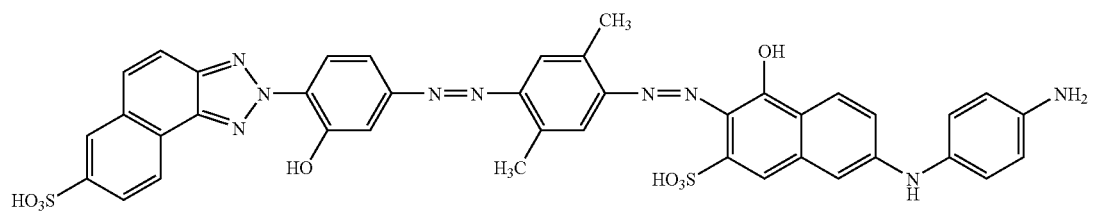
(16)
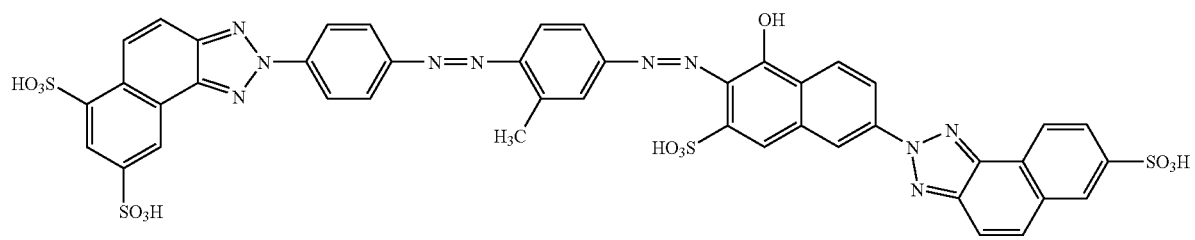
(17)
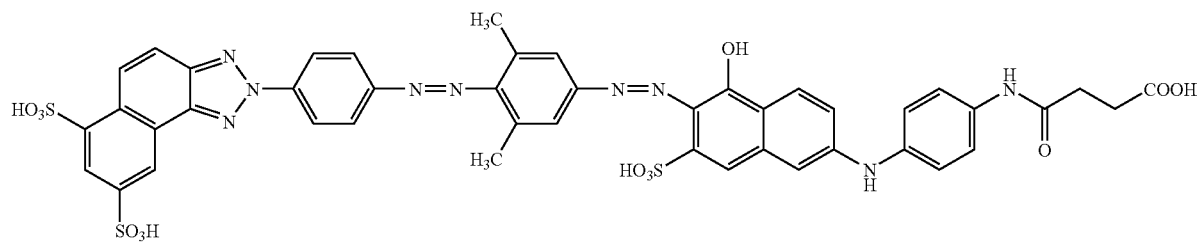
(18)
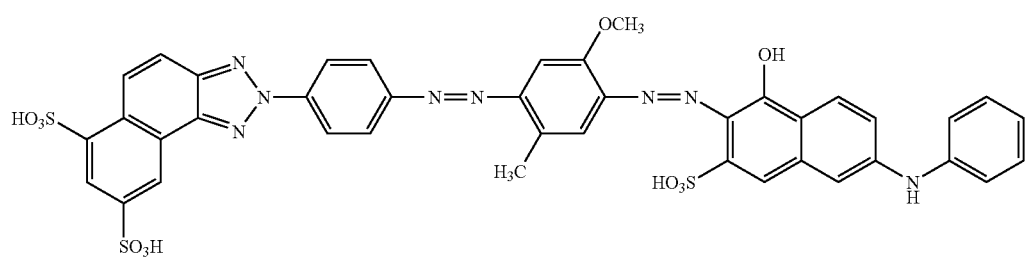

-continued
(19)
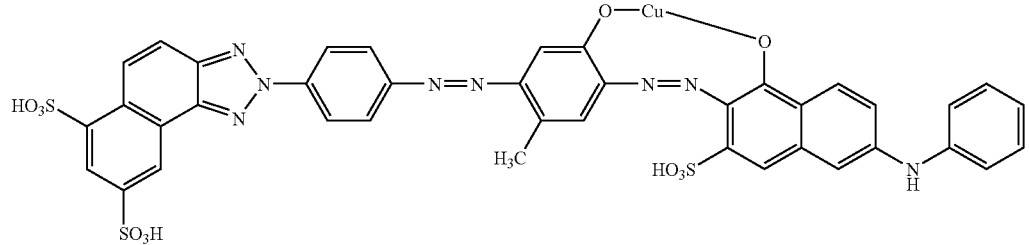
(20)
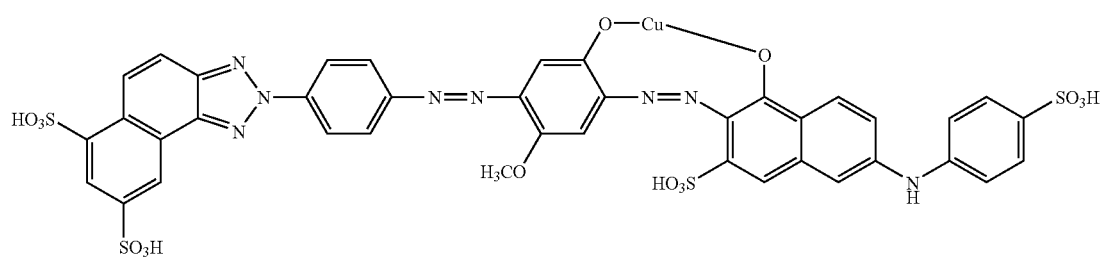
(21)
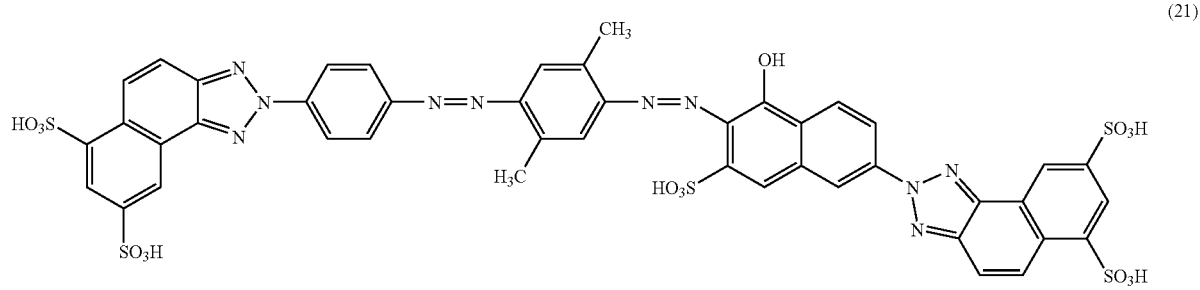
(22)
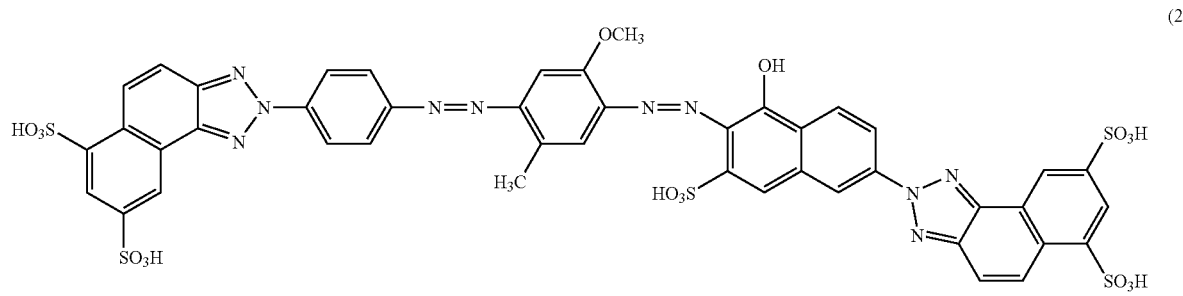
(23)
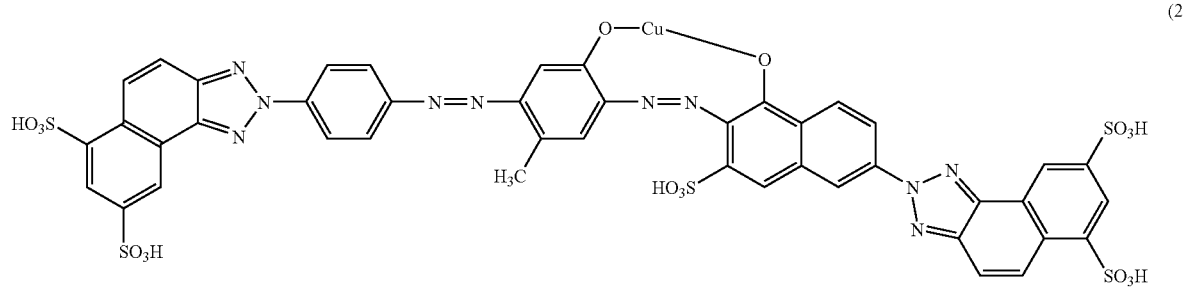
(24)
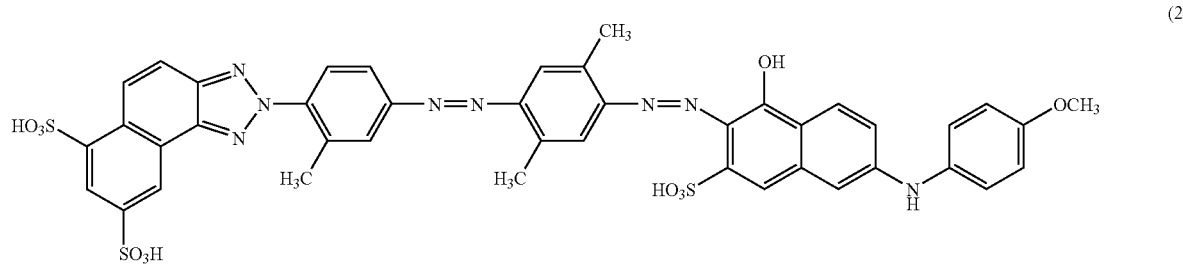

-continued
(25)
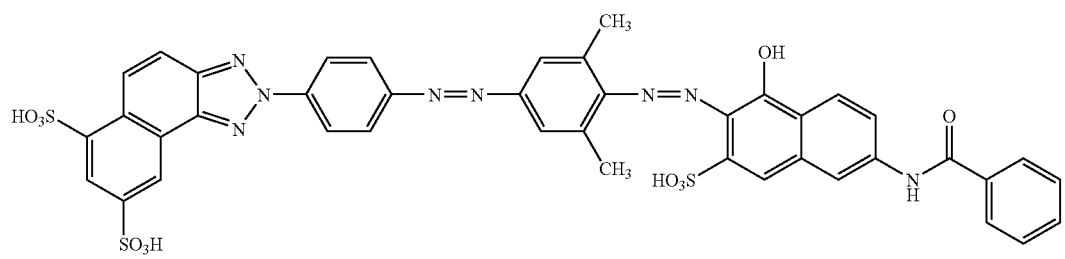
(26)
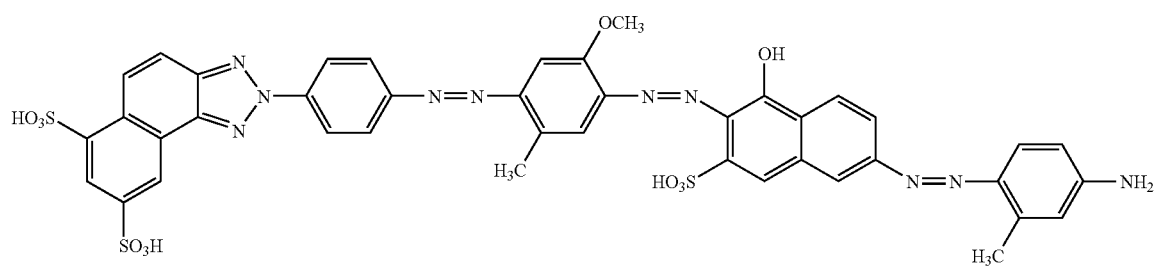
(27)
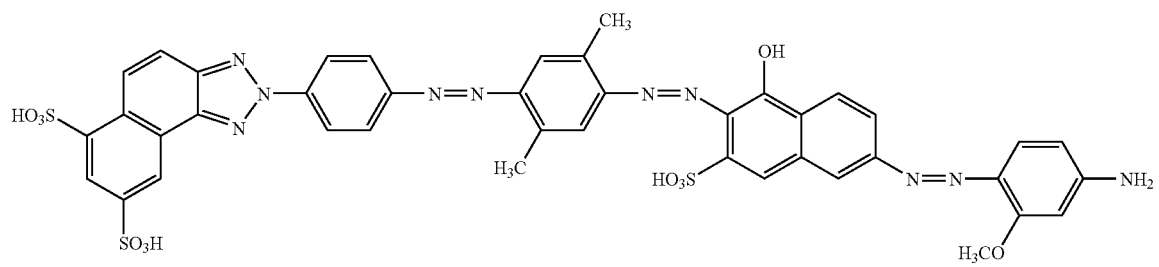
(28)
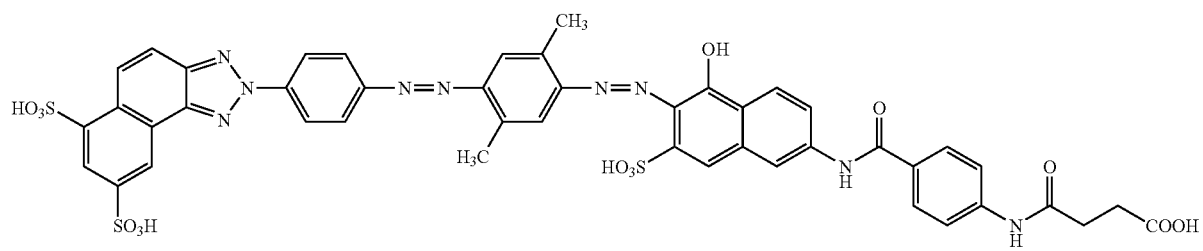
(29)
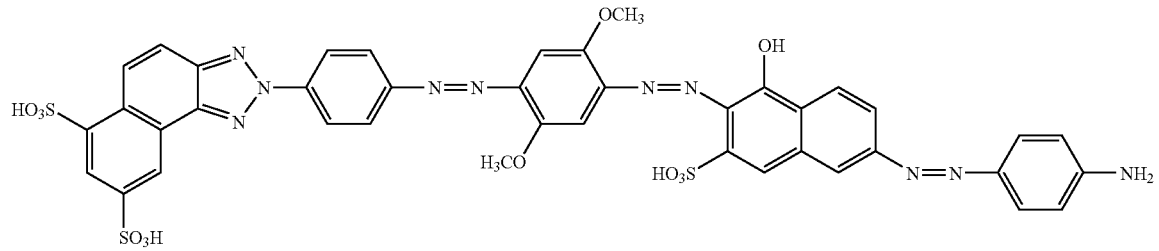
(30)
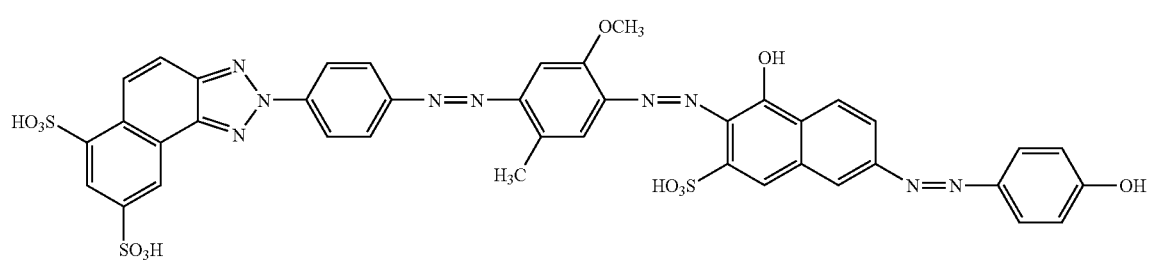

(31)
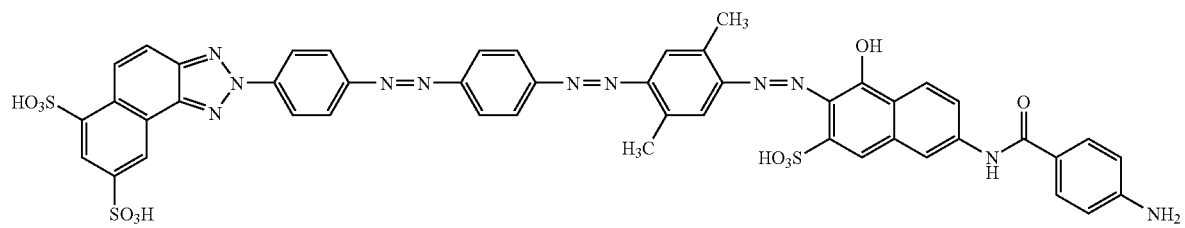
(32)
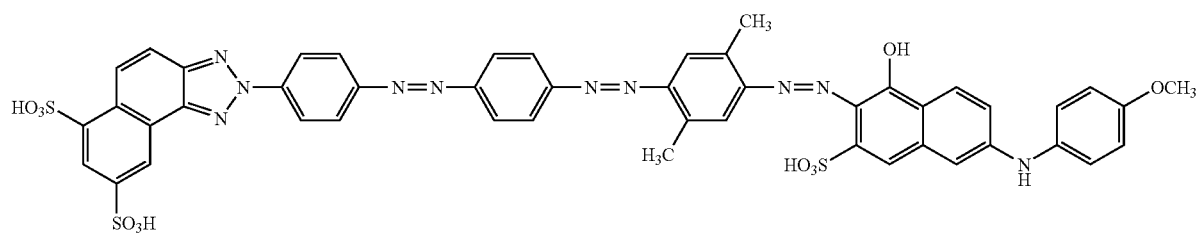
(33)
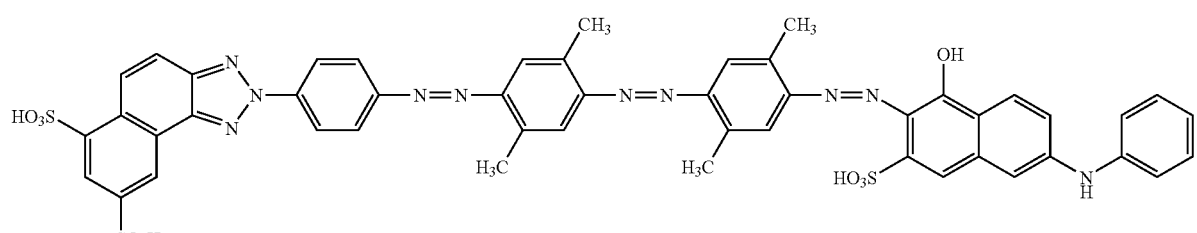
(34)
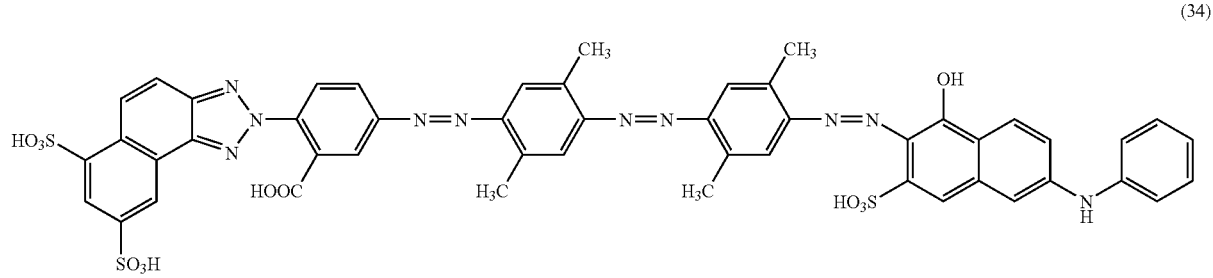
(35)
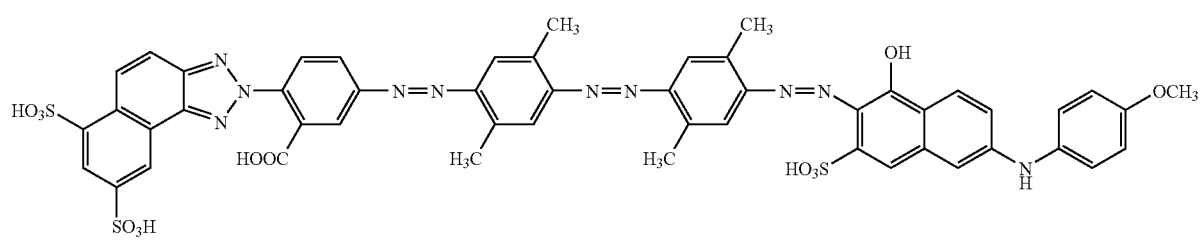
(36)
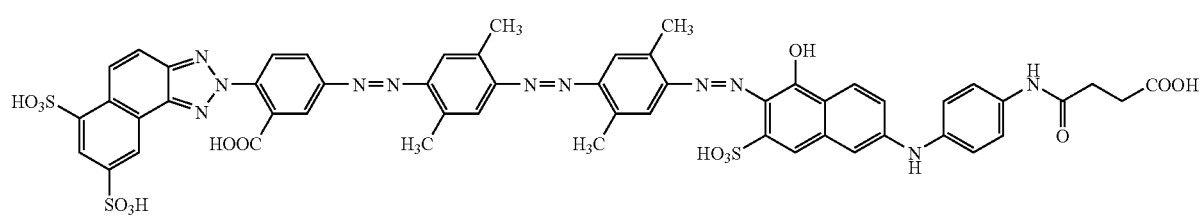

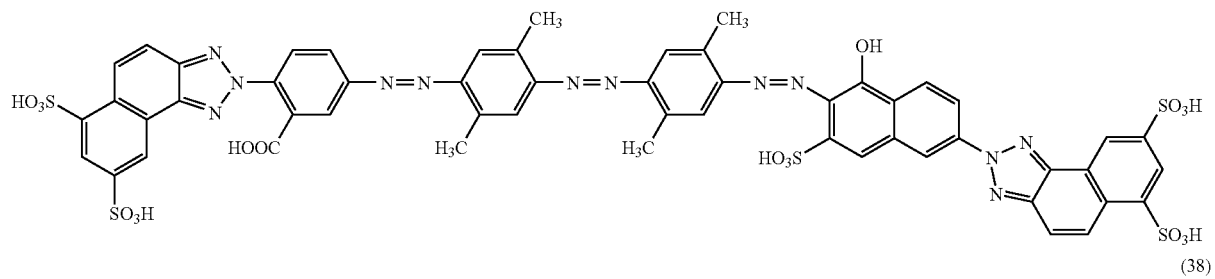

(37)

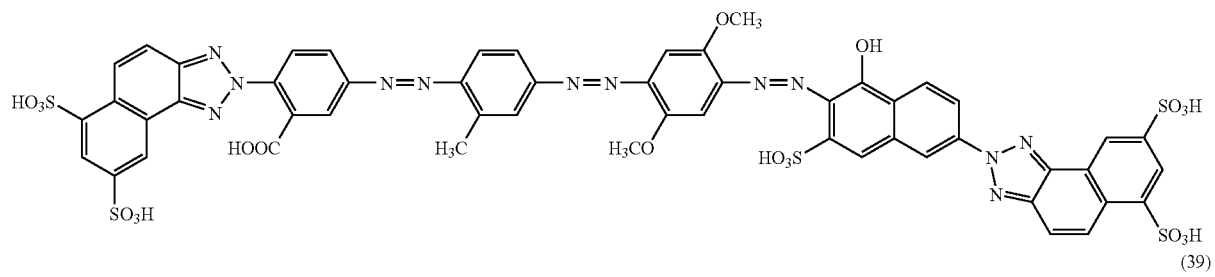

(38)

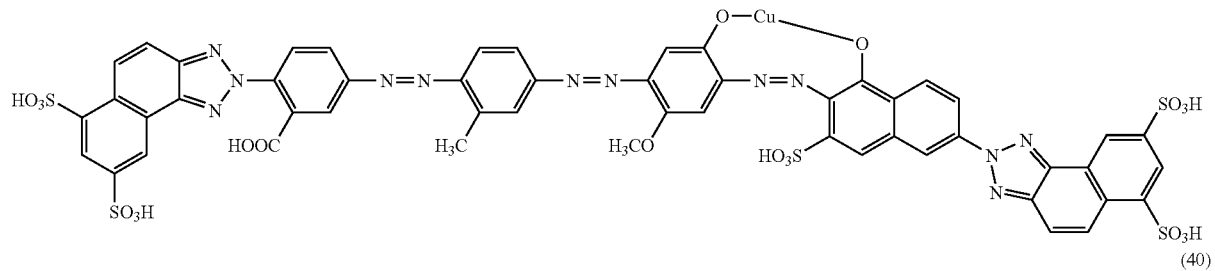

(39)

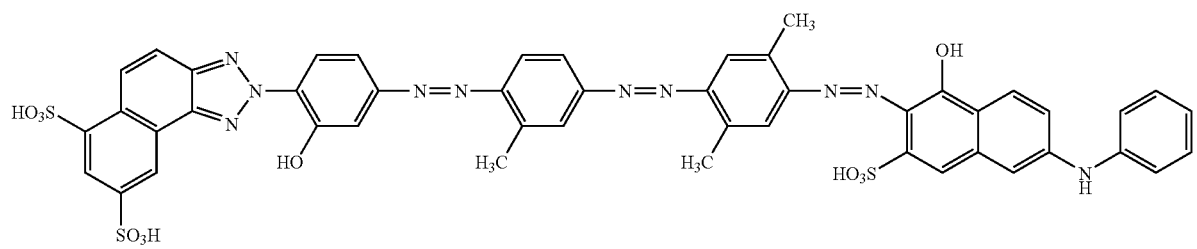

(40)

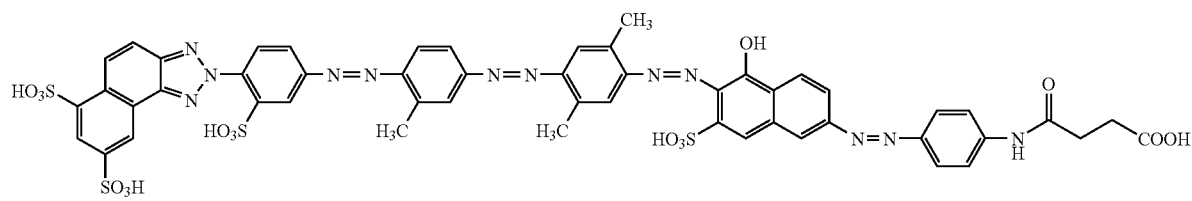

(41)

The azo compound represented by the formula (1) or a salt thereof can easily be produced by carrying out heretofore known diazotization and coupling reactions according to a production method of common azo dyes such as described in Non-Patent Document 1. As a specific production method, an N-(4-aminophenyl)acetamide represented by the following formula (A) is diazotized and, then, coupled with naphthalene sulfonic acid represented by the following formula (B); the obtained monoazoamino compound [the following formula (C)] is oxidized, then converted to a triazole, and, thereafter, hydrolyzed to obtain a compound represented by the following formula (D).

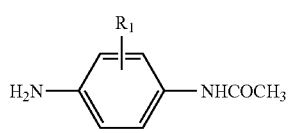

(A)

wherein $R_1$ represents the same meaning as in the formula (1).

(B)

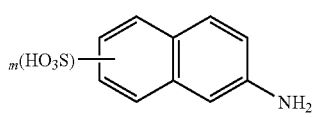

wherein m represents the same meaning as in the formula (1).

(C)

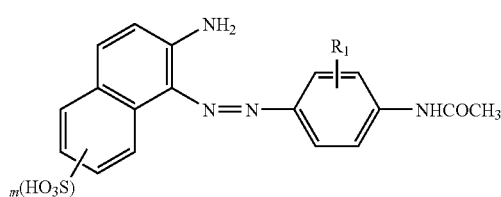

(D)

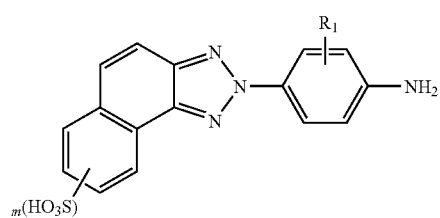

wherein $R_1$ and m represent the same meanings as in the formula (1).

Subsequently, the compound represented by the formula (D) is diazotized and subjected to primary coupling with an aniline represented by the following formula (E) to obtain a monoazoamino compound represented by the following formula (F).

(E)

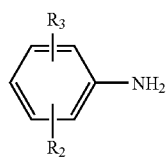

wherein $R_2$ and $R_3$ represent the same meanings as in the formula (1).

(F)

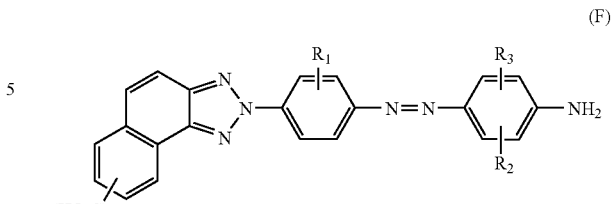

Subsequently, this monoazoamino compound is diazotized and subjected to secondary coupling with an aniline represented by the following formula (G) to obtain a disazoamino compound represented by the following formula (H).

(G)

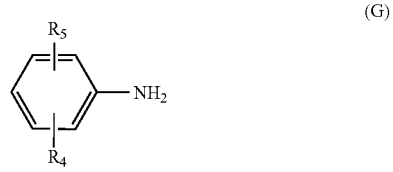

wherein $R_4$ and $R_5$ represent the same meanings as in the formula (1).

(H)

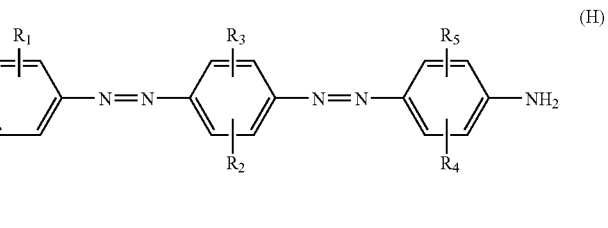

This disazoamino compound is diazotized and subjected to tertiary coupling with a naphthol represented by the following formula (I) to obtain the azo compound represented by the formula (1).

(I)

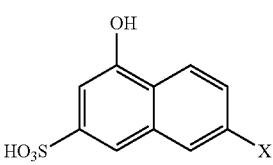

wherein X represents the same meaning as in the formula (1).

In the reaction described above, the diazotization step is carried out according to a usual method of mixing a nitrite salt such as sodium nitrite into a solution or a suspension of a diazo component in an aqueous solution of a mineral acid such as hydrochloric acid or sulfuric acid, or the step is carried out according to a reverse method where a nitrite salt is added beforehand to a neutral or weakly alkaline aqueous solution of the diazo component and this solution is mixed with the mineral acid. The temperature of diazotization is suitably −10 to 40° C. Further, the coupling step with an aniline is carried out by mixing an acidic aqueous solution such as hydrochloric acid or acetic acid with the respective above-mentioned diazo solutions and reacting at a temperature of −10 to 40° C. under an acidic condition of pH 2 to 7.

The monoazo compound and disazo compound obtained by coupling may be taken out by filtering as they are or after precipitation by addition of an acid or a salt. Alternatively, they may be subjected to the next step as they are, in the form of a solution or a suspension. When the diazonium salt is hardly soluble and exists as a suspension, the salt may be collected by filtration and used as a press cake in the subsequent coupling step.

The triazole formation step in the aforementioned reactions is carried out, for example, according to a method described in "Dyestuff Chemistry" by Yutaka Hosoda (Published by Gihodo Co., Ltd.) p. 635, by adding sodium hypochlorite or aqueous ammonia/copper sulfate to an aqueous solution of an azo compound.

The tertiary coupling reaction between the diazotized material of the disazoamino compound and the naphthol represented by the formula (I) is carried out at a temperature between −10 to 40° C. and at a neutral to alkaline condition of pH 7 to 10. After the reaction is complete, the reaction product may be precipitated by salting out and taken out by filtration. In addition, when purification is necessary, the operation of salting out is repeated or the product is precipitated from water using an organic solvent. The organic solvents to be used in purification include water-soluble organic solvents, for example, alcohols such as methanol and ethanol and ketones such as acetone.

Note that in the present invention, the azo compound represented by the formula (1) may be used as a free acid or a salt of the azo compound may also be used. Examples of such salts include an alkali metal salt such as a lithium salt, a sodium salt, or a potassium salt; an ammonium salt; and an organic salt such as an amine salt. Generally, the sodium salt is used. Further, depending on the situation, a copper complex such as the one represented by the formula (2) may also be used, the complex being obtained by complex formation according to a conventional method of adding copper sulfate and the like to the azo compound or a salt thereof.

The substituent of the N-(4-aminophenyl)acetamide (the above-described formula (A)) which is the starting material for synthesis of the water-soluble dye represented by the formula (1) and may have a substituent $R_1$ includes a hydrogen atom, a methyl group, an ethyl group, a methoxy group, an ethoxy group, an acetylamino group, a sulfonic acid group, a carboxyl group, a hydroxyl group, and the like. Phenylene diamines include, for example, 1,4-phenylenediamine, 2,5-diaminotoluene, 2,5-diaminobenzenesulfonic acid, 2,5-diaminobenzoic acid, and 2,5-diaminophenol, where 1,4-phenylenediamine and 2,5-diaminobenzoic acid are preferable. A substituent of the naphthalene sulfonic acid (the above-described formula (B)), which is coupled first, includes a hydrogen atom or a sulfonic acid group. The naphthalene sulfonic acid includes, for example, 6-aminonaphthalene-2-sulfonic acid, 6-aminonaphthalene-3-sulfonic acid, 7-aminonaphthalene-1,3-disulfonic acid, 6-aminonaphthalene-1,3-disulfonic acid, and the like, of which 6-aminonaphthalene-1,3-disulfonic acid is preferable.

Each of the substituents of anilines (the above-described formula (E) or (G)), which are the primary and secondary coupling components and may have substituents ($R_2$ to $R_5$), preferable is a hydrogen atom, a methyl group, an ethyl group, a methoxy group, an ethoxy group, or an acetylamino group, of which a hydrogen atom, a methyl group, or a methoxy group is more preferable. One or two of these substituents may be bound to each other. The anilines include, for example, aniline, 2-methylaniline, 3-methylaniline, 2-ethylaniline, 3-ethylaniline, 2,5-dimethylaniline, 2,5-diethylaniline, 2-methoxyaniline, 3-methoxyaniline, 2-methoxy-5-methylaniline, 2,5-dimethoxyaniline, 3,5-dimethyl aniline, 2,6-dimethylaniline, or 3,5-dimethoxyaniline. The amino group of these anilines may be protected. The protecting group includes, for example, an ω-methanesulfonic acid group thereof. The anilines used in the primary coupling and those used in the secondary coupling may be the same or different.

X in the naphthol (the above-described formula (I)) containing X, which is the tertiary coupling component includes a benzoylamino group which may have one or more substituents, a phenylamino group which may have one or more substituents, a phenylazo group which may have one or more substituents, or a naphthotriazole group which may have one or more substituents. Each of the one or more substituents is preferably a hydrogen atom, a lower alkyl group, a lower alkoxyl group, a hydroxyl group, a carboxyl group, a sulfonic acid group, a nitro group, an amino group, or a substituted amino group.

When X is a naphthotriazole group which may have one or more substituents, preferable is the naphthotriazole group represented by the formula (3) and having substituents ($R_6$, $R_7$). More preferably, each of the substituents ($R_6$ and $R_7$) is a hydrogen atom or a sulfonic acid group. The positions of substitution are preferably the 6- and 8-positions of the naphthalene ring.

When X is a benzoylamino group which may have one or more substituents, preferable is the benzoylamino group represented by the formula (4) and having a substituent ($R_8$). More preferably, the substituent ($R_8$) is a hydrogen atom, an amino group, or a substituted amino group. The positions of substitution are preferably the 2-, 3-, and 4-positions in relation to the amino group. Above all, the 4-position is more preferable.

When X is a phenylamino group which may have one or more substituents, preferable is the phenylamino group represented by the formula (5) and having substituents ($R_9$, $R_{10}$). More preferably, each of the substituents ($R_9$ and $R_{10}$) is a hydrogen atom, a methyl group, a methoxy group, a sulfonic acid group, an amino group, or an amino group which may have one or more substituents. The positions of substitution are preferably the 2- and 4-positions, or 3- and 4-positions. Above all, the 2- and 4-positions are more preferable.

When X is a phenylazo group which may have one or more substituents, preferable is the phenylazo group represented by the formula (6) and having substituents ($R_{11}$, $R_{12}$). More preferably, each of the substituents ($R_{11}$ and $R_{12}$) is a hydrogen atom, a methyl group, a methoxy group, an amino group, a substituted amino group, or a hydroxyl group. When one of the substituents is a hydrogen atom and another is other substituent, the position of substitution of the other substituent is preferably the 2-, 3-, or 4-position relative to the azo group. When both substituents are ones other than a hydrogen atom, the positions of both are preferably the 2- and 4-positions, or 3- and 5-positions. Above all, the 2- and 4-positions are more preferable.

In the formula (1), m represents 1 or 2, and n represents 0 or 1. Especially preferably, m is 2. Note that the sulfonic acid group, the carboxylic acid group, and the hydroxyl group in the formula are shown in the form of a free acid.

Further, in the dye-containing polarizing film or dye-containing polarizing plate of the present invention, the azo compound represented by the formula (1) or (2), a salt thereof, or a copper complex compound of either of these may be used singly or, as necessary, together with one or more kinds of other organic dyes. There is no particular restriction on the organic dyes which are used together but they are preferably dyes having absorption characteristics in wavelength ranges different from the absorption wavelength ranges of the azo compounds or salts thereof of the present invention or copper complexes of any of them and having high dichroism. Examples include C.I. Direct Yellow 12, C.I. Direct Yellow 28, C.I. Direct Yellow 44, C.I. Direct Orange 26, C.I. Direct Orange 39, C.I. Direct Orange 71, C.I. Direct Orange 107, C.I. Direct Red 2, C.I. Direct Red 31, C.I. Direct Red 79, C.I. Direct Red 81, C.I. Direct Red 247, C.I. Direct Green 80, C.I. Direct Green 59, and the dyes described in Patent Documents 1 to 6. These dyes are used as free acids, alkali metal salts (for example, Na salts, K salts, Li salts), ammonium salts, or amine salts.

When other organic dyes are used together as necessary, the kind of the dye blended varies depending on whether the intended polarizing film is a neutral color polarizing film, a color polarizing film for a liquid crystal projector, or other color polarizing film. The blending ratio thereof is not particularly limited, but generally, one or more kinds of the above organic dyes are preferably used in a total amount in a range of 0.1 to 10 parts by weight based on the weight of the azo compound of the formula (1) or (2) or a salt thereof.

A polarizing film having various hues and a neutral color, used for the dye-containing polarizing film or the polarizing plate for a liquid crystal projector of the present invention can be prepared by incorporating the azo compounds represented by the formula (1) or (2), or a salt thereof together with other organic dyes as necessary into a polymer film, which is a material for the polarizing film, by a publicly known method. To the polarizing film obtained is attached a protective film to produce a polarizing plate, and as necessary, a protecting layer or an AR (anti-reflection) layer, a support, and the like are disposed thereon, to be used for a liquid crystal projector, an electronic calculator, a watch, a notebook computer, a word processor, a liquid crystal television, a car navigation system, indoor and outdoor measurement instruments, a display, and the like.

As the polarizing film substrates (polymer films) used for the dye-containing polarizing film of the present invention, polyvinyl alcohol substrates are preferable. The polyvinyl alcohol substrates include, for example, polyvinyl alcohol or a derivative thereof, and those obtained by modifying either of these with an olefin such as ethylene or propylene; an unsaturated carboxylic acid such as crotonic acid, acrylic acid, methacrylic acid, or maleic acid; and the like. Among these, a film comprising polyvinyl alcohol or a derivative thereof is preferably used from the standpoint of a dye adsorption property and an orientation property. The thickness of the substrate is usually 30 to 100 µm, preferably about 60 to 90 µm.

In incorporating the azo compound of the formula (1) or (2) and/or a salt thereof into such a polarizing film substrate (polymer film), usually, a method of dyeing the polymer film is adopted. Dyeing, for example, is carried out as follows. First, the azo compound and/or a salt thereof of the present invention, and other dyes as necessary, are dissolved in water to prepare a dye bath. The concentration of dyes in the dye bath is not particularly limited but usually selected from a range of about 0.001 to 10% by weight. Furthermore, a dyeing auxiliary may be used as necessary and, for example, sodium sulfate is suitably used in a concentration of about 0.1 to 10% by weight. Dyeing is carried out by dipping the polymer film in the dye bath thus prepared for 1 to 10 minutes. The dyeing temperature is preferably about 40 to 80° C.

Orientation of the water-soluble dye is carried out by stretching the polymer film dyed as described above. As a stretching method, any publicly known method may be employed, such as, for example, a wet method and a dry method. In some cases, stretching of the polymer film may be carried out before dyeing. In this case, orientation of the water-soluble dye is performed at the time of dyeing. The polymer film in which the water-soluble dye is incorporated and oriented is, as necessity, subjected to an after-treatment such as a boric acid treatment by a publicly known method. Such an after-treatment is carried out in order to improve light transmittance and degree of polarization of the polarizing film. The condition of the boric acid treatment varies depending on the kind of polymer film used and the kind of dye used. In general, the concentration of boric acid in its aqueous solution is in a range of 0.1 to 15% by weight, preferably 1 to 10% by weight, and the treatment is carried out by dipping at a temperature range of 30 to 80° C., preferably 40 to 75° C., for 0.5 to 10 minutes. Further, as necessary, the polymer film may simultaneously be subjected to a fixing treatment with an aqueous solution containing a cationic polymer compound.

To one or both surfaces of the dye-containing polarizing film of the present invention thus obtained, transparent protective films having excellent optical transparency and mechanical strength may be adhered to produce a polarizing plate. As a material to form the protective film, there may be used, for example, a cellulose acetate film, an acrylic film, a fluorinated film such as a tetrafluoroethylene/hexafluoropropylene copolymer, and a film composed of a polyester resin, a polyolefin resin, or a polyamide resin. Preferably, a triacetyl cellulose (TAC) film or a cycloolefin film may be used. The thickness of the protective film is usually 40 to 200 µm.

An adhesive which may be used to adhere the polarizing film and the protective film together includes a polyvinyl alcohol (PVA) adhesive, an urethane emulsion adhesive, an acrylic adhesive and a polyester-isocyanate adhesive. Of these, the polyvinyl alcohol adhesive is suitable.

Furthermore, a transparent protective layer may be provided on the surface of the dye-containing polarizing plate of the present invention. The protective layer includes, for example, an acrylic or polysiloxane hard coat layer and a urethane protective layer. In addition, in order to further improve the single plate light transmittance, it is preferable to provide an AR layer on this protective layer. The AR layer may be formed, for example, by a vapor deposition or sputtering of a substance such as silicon dioxide or titanium dioxide. The AR layer may also be formed by thinly coating a fluorinated substance. Additionally, the dye-containing polarizing plate of the present invention may also be used as an elliptically polarizing plate having a phase difference plate adhered.

The dye-containing polarizing plate of the present invention thus constituted has a neutral color, causes no color leakage at the perpendicular position in the wavelength range of visible light, and shows excellent polarization performance. Further, it has characteristics that, even under conditions of high temperatures and high humidity, it shows no discoloration, no deterioration of polarization performance, and little light leakage at the perpendicular position in the range of visible light.

In the present invention, the color polarizing plate for a liquid crystal projector includes, as a dichroic molecule, the azo compound represented by the formula (1) or (2) and/or a salt thereof and further, as necessary, other organic dyes mentioned above. Also, the polarizing film used for the color polarizing plate for a liquid crystal projector of the present invention is produced by the same method as that described for producing the dye-containing polarizing film of the present invention. A protective film is further attached to the polarizing film to produce a polarizing plate, which is, as necessary, provided with a protective layer or an AR layer, a support, and the like, and is used as the color polarizing plate for a liquid crystal projector.

As the color polarizing plate for a liquid crystal projector, preferably, the single plate average light transmittance is 39% or higher and the average light transmittance at perpendicular position is 0.4% or less in the wavelength range necessary for the polarizing plate (A. Examples of the peak wavelengths when an ultra-high pressure mercury lamp is used: 420 to 500 nm for the blue channel, 500 to 580 nm for the green channel, and 600 to 680 nm for the red channel; B. Examples of the peak wavelengths when three primary color LED lamps are used: 430 to 450 nm for the blue channel, 520 to 535 nm for the green channel, 620 to 635 nm for the red channel). More preferably, in the wavelength range necessary for the polarizing plate, the single plate average light transmittance is 41% or higher and the average light transmittance at the perpendicular position is 0.3% or less, more preferably 0.2% or less. Especially preferably, in the wavelength range necessary for the polarizing plate, the single plate average light transmittance is 42% or higher and the average light transmittance at the perpendicular position is 0.1% or less. As mentioned above, the color polarizing plate for a liquid crystal projector of the present invention has brightness and excellent polarization performance.

The color polarizing plate for a liquid crystal projector of the present invention is preferably a polarizing plate with an AR layer, which is obtained by providing the above-mentioned AR layer on a polarizing plate comprising a polarizing film and a protective film. Further, a polarizing plate with an AR layer and a support is more preferable, which is obtained by adhering the polarizing plate with an AR layer to a support such as a transparent glass plate.

In addition, the single plate average light transmittance is an average value of light transmittance in a specific wavelength range when natural light enters one polarizing plate without either AR layer or such a support as a transparent glass plate provided (hereafter, simply referred to as a "polarizing plate" in the same sense). The average light transmittance at the perpendicular position is an average value of light transmittance in a specific wavelength range when natural light enters two polarizing plates, which are superimposed with the orientation directions perpendicular to each other.

The color polarizing plate for a liquid crystal projector of the present invention is used usually as a polarizing plate with a support. The support preferably has a planar section because a polarizing plate is adhered thereto. Also, the support is preferably a molded article of glass because the polarizing plate is used in an optical application. The molded article of glass, for example, a glass plate, a lens, a prism (for example, a triangle prism or a cubic prism). A lens to which is adhered the polarizing plate may be used as a condenser lens with a polarizing plate in a liquid crystal projector. Also, a prism to which is adhered the polarizing plate may be used in a liquid crystal projector as a polarizing beam splitter with a polarizing plate or as a dichroic prism with a polarizing plate. Further, the polarizing plate may be adhered to a liquid crystal cell. A material of glass includes inorganic glass such as soda glass, borosilicate glass, and sapphire glass; organic glass such as acrylic and polycarbonate; and the like. Preferable is the inorganic glass. The thickness and size of a glass plate may be chosen as desired. Also, in order to further improve the single plate light transmittance of the polarizing plate with glass attached, it is preferable to provide an AR layer on one or both sides of the glass surface and polarizing plate surface.

In order to produce a color polarizing plate with a support for a liquid crystal projector, for example, a transparent adhesive (pressure-sensitive adhesive) is coated on the planar section of the support and then the dye-containing polarizing plate of the present invention is attached to this coated surface. Also, the transparent adhesive (pressure-sensitive adhesive) may be coated on the polarizing plate and then a support may be attached to this coated surface. As the adhesive (pressure-sensitive adhesive) used herein, for example, an acrylic ester adhesive is preferable. Note that when this polarizing plate is used as an elliptically polarizing plate, usually a phase difference plate side is adhered to the support, but the polarizing plate side may be adhered to the molded article of glass.

In a color liquid crystal projector using the dye-containing polarizing plate of the present invention, the dye-containing polarizing plate of the present invention is disposed on either one or both of the incident side and outgoing side of the liquid crystal cell. The polarizing plate may or may not be in contact with the liquid crystal cell, but, in terms of durability, it is preferable that the plate be not in contact with the cell. When the polarizing plate is in contact with the liquid crystal cell at the outgoing side, a dye-containing polarizing plate of the present invention having the liquid crystal cell can be used as a support. When the polarizing plate is not in contact with the liquid crystal cell, it is preferable to use the dye-containing polarizing plate of the present invention, which uses a support other than the liquid crystal cell. Furthermore, in terms of durability, it is preferable that the dye-containing polarizing plates of the present invention be disposed on both the incident side and outgoing side of the liquid crystal cell. Further, it is preferable that the polarizing plate surface of the dye-containing polarizing plate of the present invention be disposed on the liquid crystal cell side, with the support surface thereof on the light source side. In addition, the incident side of the liquid crystal cell means the light source side, and the opposite side is referred to as the outgoing side.

In a color liquid crystal projector using the dye-containing polarizing plate of the present invention, an ultraviolet light-cutting filter is preferably disposed between the light source and the aforementioned polarizing plate with a support on the incident side. Further, the liquid crystal cell used is preferably, for example, an active matrix type, which is formed by encapsulating liquid crystals between a transparent substrate, on which an electrode and a TFT are formed, and another transparent substrate, on which the counter electrode is formed. Light emitted from a light source such as an ultra-high pressure mercury lamp (UHP lamp), a metal halide lamp, and a white LED passes through the ultraviolet light-cutting filter, separates into three primary colors, and, thereafter, passes through the respective color polarizing plates with supports for each of the blue, green, and red channels. The light is then integrated, magnified by a projector lens, and projected onto a screen. Alternatively, using LEDs corresponding to each of blue, green, and red colors, light emitted from LED of each color passes through the respective color polarizing plates with supports for each of blue, green, and red channels, then is integrated, magnified by a projector lens, and projected onto a screen.

The color polarizing plate for a liquid crystal projector thus constituted has characteristics that its polarization performance is excellent, and, furthermore, discoloration and deterioration of polarization performance do not occur even under conditions of high temperature and high humidity.

EXAMPLES

Hereinafter, the present invention will be described in more detail by way of examples. However, these are for illustrative purposes only and not meant to limit the scope of the present invention in any manner. In the examples, % and parts are based on weight unless otherwise noted.

Example 1

To 150 parts of water was added 15 parts of N-(4-aminophenyl)acetamide. After cooling to 10° C. or lower, 52 parts of 35% hydrochloric acid and then 7.1 parts of sodium nitrite were added thereto, and the reaction mixture was stirred at 5 to 10° C. for 1 hour. To this was added 31.2 parts of 6-aminonaphthalene-1,3-disulfonic acid dissolved in water and the pH was adjusted to 3 by addition of sodium carbonate while stirring. By further stirring, the coupling reaction was completed and, thereafter, 24 parts of sodium hypochlorite was added. The reaction mixture was stirred at 70° C. for 2 hours to form a triazole. This compound was added to 300 parts of water, followed by addition of 105 parts of 35% hydrochloric acid. The mixture was stirred at 90° C. for 2 hours to complete hydrolysis to obtain 30 parts of a compound represented by the following formula (42).

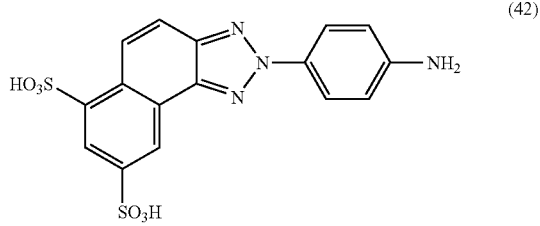

(42)

After dispersing 30 parts of the compound represented by the formula (42) in 150 parts of water, the compound was dissolved with sodium hydroxide and diazotized by adding 5.0 parts of sodium nitrite and then 36.5 parts of 35% hydrochloric acid, and stirring at 20 to 30° C. for 2 hours. To the reaction mixture, 13.4 parts of phenylaminomethanesulfonic acid was added and, while stirring at 20 to 30° C., the pH was adjusted to 3 by addition of sodium carbonate. By further stirring, the coupling reaction was completed and, thereafter, this monoazo compound was added to 300 parts of water. Thereto was added 12 parts of sodium hydroxide and the reaction mixture was stirred at 90° C. for 2 hours to complete hydrolysis. There was obtained 26.2 parts of a monoazo compound represented by the following formula (43).

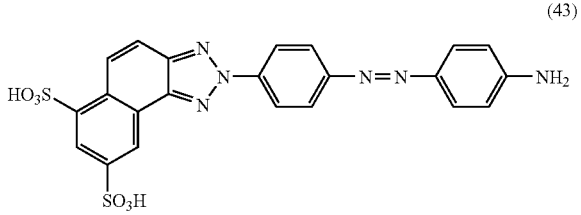

(43)

After dispersing 26.2 parts of the monoazo compound represented by the formula (43) in 300 parts of water, the compound was dissolved with sodium hydroxide and diazotized by adding 3.6 parts of sodium nitrite and then 26 parts of 35% hydrochloric acid, and stirring at 25 to 30° C. for 2 hours. Meanwhile, 28.4 parts of a compound represented by the following formula (44) was added to 300 parts of water and dissolved by making the solution weakly alkaline with sodium carbonate. To this solution was poured the diazotized material of the monoazo compound obtained above with the pH maintained in a range of 7 to 10, and the reaction mixture was stirred to complete the coupling reaction. The reaction product was salted out with sodium chloride and collected by filtration to obtain 65 parts of the disazo compound represented by the formula (7). This compound was purple-red in color and its maximum absorption wavelength in a 20% pyridine-water solution was 539 nm.

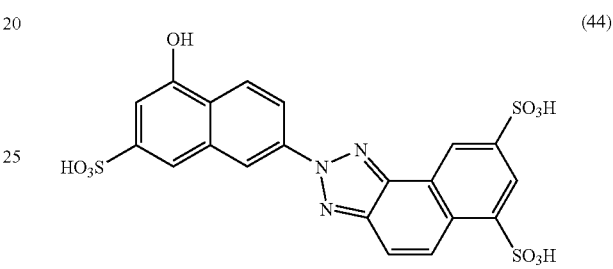

(44)

Example 2

42 parts of the compound represented by the formula (42) was diazotized in the same manner as in Example 1. To the reaction mixture, 12.0 parts of 2,5-dimethylaniline was added and, while stirring at 20 to 30° C., the pH was adjusted to 3 by addition of sodium carbonate. By further stirring, the coupling reaction was completed to obtain 44 parts of a monoazo compound represented by the following formula (45).

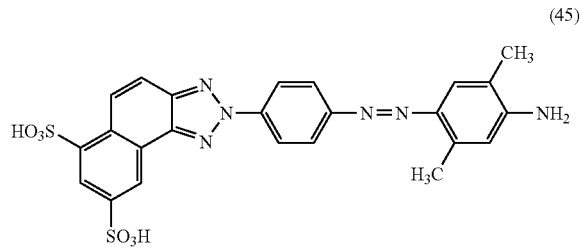

(45)

After dispersing 44 parts of the monoazo compound represented by the formula (45) in 600 parts of water, the compound was dissolved with sodium hydroxide and diazotized by adding 5.7 parts of sodium nitrite and then 41.7 parts of 35% hydrochloric acid, and stirring at 25 to 30° C. for 2 hours. Meanwhile, 26 parts of 6-phenylamino-3-sulfo-1-naphthol was added to 200 parts of water and dissolved by making the solution weakly alkaline with sodium carbonate. To this solution was poured the diazotized material of the monoazo compound obtained above with the pH maintained in a range of 7 to 10, and the reaction mixture was stirred to complete the coupling reaction. The reaction product was salted out with sodium chloride and collected by filtration to obtain 65 parts of the disazo compound represented by the formula (9). This compound was purple-red in color and its maximum absorption wavelength in a 20% pyridine-water solution was 566 nm.

Example 3

Except that the coupler in the synthesis of the compound represented by the formula (45) was changed from 2,5-dimethylaniline to 2-methoxy-5-methylaniline, 40 parts of the disazo compound represented by the formula (18) was obtained in the same manner as in Example 2. This compound was purple in color and its maximum absorption wavelength in a 20% pyridine-water solution was 576 nm.

Example 4

8.9 parts of the compound represented by the formula (18) was dissolved in 100 parts of water. To the solution, 1.6 parts of crystalline copper sulfate and 0.67 part of monoethanolamine were added, and reacted at 95° C. for 10 hours. The reaction product was salted out with sodium chloride and collected by filtration to obtain 7.5 parts of the compound represented by the formula (19). This compound was blue in color and its maximum absorption wavelength in a 20% pyridine-water solution was 622 nm.

Example 5

Except that the final coupler in the synthesis of the compound represented by the formula (9) was changed from 6-phenylamino-3-sulfo-1-naphthol to 6-(4'-methoxyphenyl)amino-3-sulfo-1-naphthol, 7.6 parts of the disazo compound represented by the formula (18) was obtained in the same manner as in Example 2. This compound was bluish-purple in color and its maximum absorption wavelength in a 20% pyridine-water solution was 569 nm.

Example 6

Except that the raw material in the synthesis of the compound represented by the formula (42) was changed from N-(4-aminophenyl)acetamide to N-(2-methyl-4-aminophenyl)acetamide, 43 parts of a compound represented by the following formula (46) was obtained in the same manner as in Example 1.

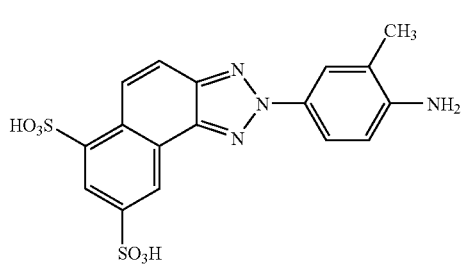

(46)

Except that the compound represented by the formula (42) was changed to the compound represented by the formula (46), 66 parts of the compound represented by the formula (12) was obtained in the same manner as in Example 2. This compound was purple-red in color and its maximum absorption wavelength in a 20% pyridine-water solution was 564 nm.

Example 7

Except that the raw material in the synthesis of the compound represented by the formula (42) was changed from N-(4-aminophenyl)acetamide to 5-acetamide-2-aminobenzoic acid, 37.1 parts of a compound represented by the formula (47) was obtained in the same manner as in Example 1.

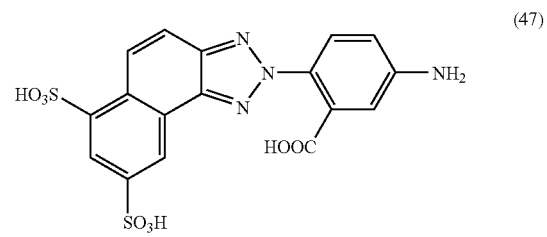

(47)

Except that the compound represented by the formula (42) was changed to the compound represented by the formula (47), 38.1 parts of a compound represented by the following formula (48) was obtained in the same manner as in Example 2.

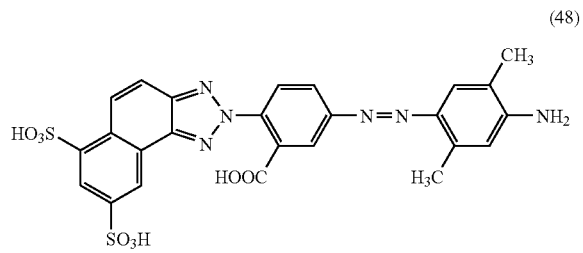

(48)

Except that the compound represented by the formula (45) was changed to the compound represented by the formula (48), 47.2 parts of the compound represented by the formula (13) was obtained in the same manner as in Example 2. This compound was purple-red in color and its maximum absorption wavelength in a 20% pyridine-water solution was 565 nm.

Example 8

Except that the final coupler in the synthesis of a compound represented by the formula (9) was changed from 6-phenylamino-3-sulfo-1-naphthol to 6-(4'-aminobenzoyl)amino-3-sulfo-1-naphthol, 67 parts of a disazo compound represented by the formula (14) was obtained in the same manner as in Example 2. This compound was red color and its maximum absorption wavelength in a 20% pyridine-water solution was 552 nm.

Example 9

Except that the final coupler in the synthesis of the compound represented by the formula (18) was changed from 6-phenylamino-3-sulfo-1-naphthol to 6-(4'-hydroxyphenylazo)-3-sulfo-1-naphthol, 63 parts of the disazo compound represented by the formula (30) was obtained in the same manner as in Example 3. This compound was bluish-purple in color and its maximum absorption wavelength in a 20% pyridine-water solution was 569 nm.

Example 10

55 parts of the monoazo compound represented by the formula (45) was diazotized in the same manner as in Example 2. To the reaction mixture, 12.5 parts of 2,5-dimethylaniline dissolved in dilute aqueous hydrochloric acid was added and, while stirring at 30 to 40° C., the pH was adjusted to 3 by addition of sodium carbonate. By further stirring, the coupling reaction was completed to obtain 54.7 parts of a disazo compound represented by the following formula (49).

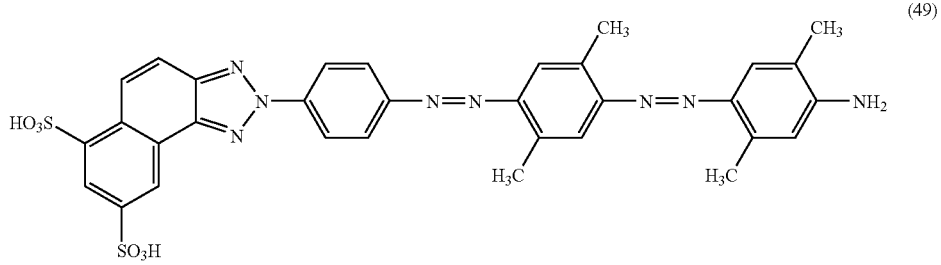

After 54.7 parts of the disazo compound represented by the formula (49) is dispersed in 500 parts of water, the compound is dissolved with sodium hydroxide and diazotized by adding 5.7 parts of sodium nitrite and then 41.7 parts of 35% hydrochloric acid, and stirring at 25 to 30° C. for 2 hours. Meanwhile, 28.4 parts of 6-phenylamino-3-sulfo-1-naphthol is added to 180 parts of water and dissolved by making the solution weakly alkaline with sodium carbonate. To this solution is poured the diazotized material of the disoazo compound obtained above with the pH maintained in a range of 7 to 10 and the reaction mixture is stirred to complete the coupling reaction. The reaction product was salted out with sodium chloride and collected by filtration to obtain 66.6 parts of the trisazo compound represented by the formula (33). This compound was purple-red in color and its maximum absorption wavelength in a 20% pyridine-water solution was 560 nm.

Example 11

47.7 parts of the monoazo compound represented by the formula (48) was diazotized in the same manner as in Example 2. To the reaction mixture, 10 parts of 2,5-dimethylaniline dissolved in dilute aqueous hydrochloric acid was added and, while stirring at 30 to 40° C., the pH was adjusted to 3 by addition of sodium carbonate. By further stirring, the coupling reaction was completed to obtain 46.6 parts of a disazo compound represented by the following formula (50).

Except that the compound represented by the formula (49) was changed to the compound represented by the formula (50), 42 parts of the trisazo compound represented by the formula (34) was obtained in the same manner as in Example 10. This compound was bluish-purple in color and its maximum absorption wavelength in a 20% pyridine-water solution was 568 nm.

Example 12

46.4 parts of the compound represented by the formula (47) was added to 500 parts of water and dissolved with sodium hydroxide. To this were added 32 parts of 35% hydrochloric acid and, then, 6.9 parts of sodium nitrite, and the reaction mixture was stirred for 1 hour. Thereto, 10.7 parts of 3-methylaniline dissolved in dilute aqueous hydrochloric acid was added and, while stirring at 20 to 30° C., the pH was adjusted to 3 by addition of sodium carbonate. By further stirring, the coupling reaction was completed to obtain 46.6 parts of a monoazo compound represented by the following formula (51).

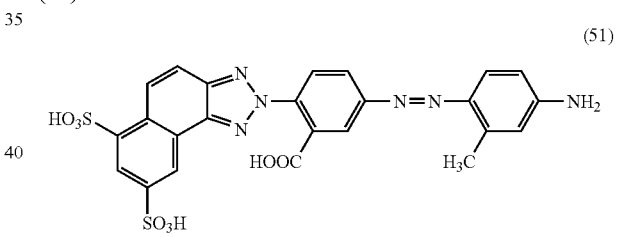

To this monoazo compound were added 25 parts of 35% hydrochloric acid and, then, 5.5 parts of sodium nitrite, and the reaction mixture was stirred for 1 hour. Thereto, 12.2 parts of 2,5-dimethoxyaniline dissolved in dilute aqueous hydrochloric acid was added and, while stirring at 30 to 40° C., the pH was adjusted to 3 by addition of sodium carbonate. By further stirring, the coupling reaction was completed to obtain 47.7 parts of a disazo compound represented by the following formula (52).

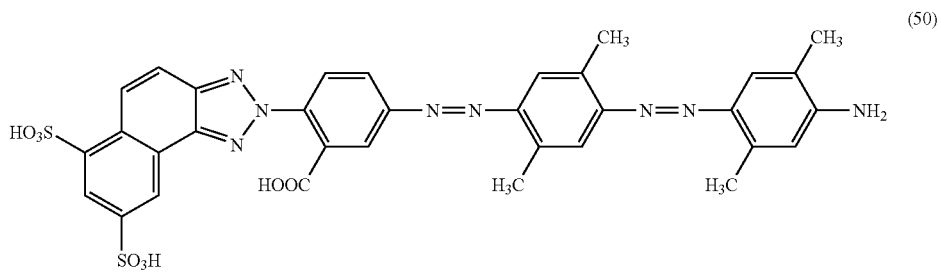

(52)

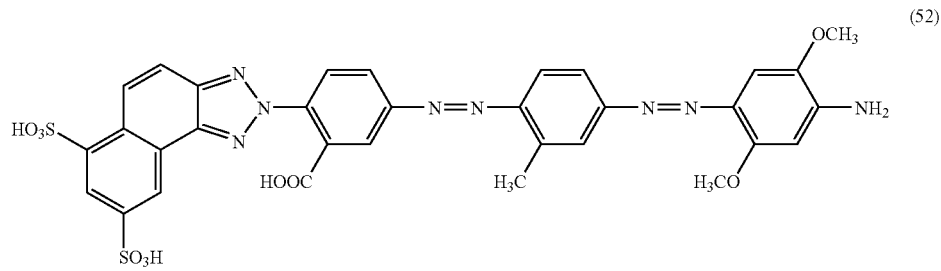

After dispersing 47.7 parts of the disazo compound represented by the formula (52) in 500 parts of water, the compound was dissolved with sodium hydroxide and diazotized by adding 3.5 parts of sodium nitrite and then 5.3 parts of 35% hydrochloric acid, and stirring at 25 to 30° C. for 2 hours. Meanwhile, 28.3 parts of the compound represented by the formula (44) was added to 300 parts of water and dissolved by making the solution weakly alkaline with sodium carbonate. To this solution was poured the diazotized material of the disazo compound obtained above with the pH maintained in a range of 7 to 10 and the reaction mixture was stirred to complete the coupling reaction. The reaction product was salted out with sodium chloride and collected by filtration to obtain 54.3 parts of a trisazo compound represented by the following formula (53).

Meanwhile, 43.0 parts of a compound represented by the formula (54) was added to 180 parts of water and dissolved by making the solution weakly alkaline with sodium carbonate. To this solution was poured the diazotized material of the disazo compound obtained above with the pH maintained in a range of 7 to 10 and the reaction mixture was stirred to complete the coupling reaction. The reaction product was salted out with sodium chloride and collected by filtration to obtain 58.5 parts of the trisazo compound represented by the formula (36). This compound was bluish-purple in color and its maximum absorption wavelength in a 20% pyridine-water solution was 577 nm.

(53)

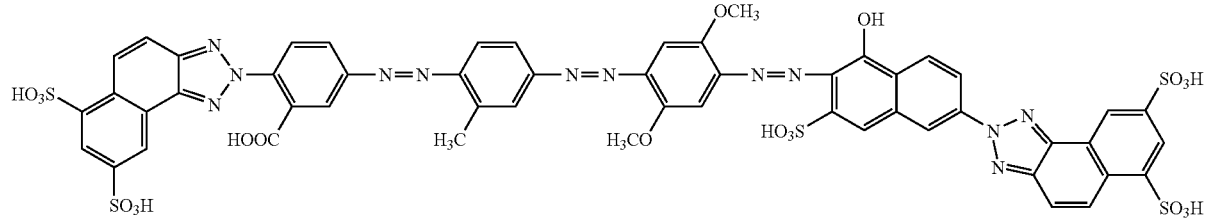

54.3 parts of the compound represented by the formula (53) was dissolved in 100 parts of water. To the solution were added 12.3 parts of crystalline copper sulfate and 25 parts of monoethanolamine and reacted at 95° C. for 10 hours. Thereafter, the reaction product was salted out with sodium chloride and collected by filtration to obtain 10 parts of the compound represented by the formula (39). This compound was green in color and its maximum absorption wavelength in a 20% pyridine-water solution was 656 nm.

(54)

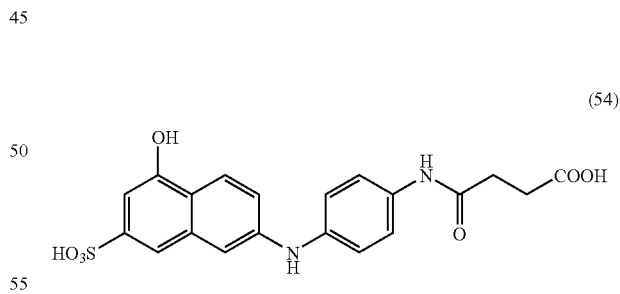

Example 13

After 72.8 parts of the disazo compound represented by the formula (50) was dispersed in 500 parts of water, the compound was dissolved with sodium hydroxide and diazotized by adding 6.9 parts of sodium nitrite and then 31.3 parts of 35% hydrochloric acid, and stirring at 25 to 30° C. for 2 hours.

Example 14

Except that the raw material in the synthesis of the compound represented by the formula (42) was changed from N-(4-aminophenyl)acetamide to N-(4-amino-3-hydroxyphenyl)acetamide, 34.9 parts of a compound represented by the following formula (55) was obtained in the same manner as in Example 1.

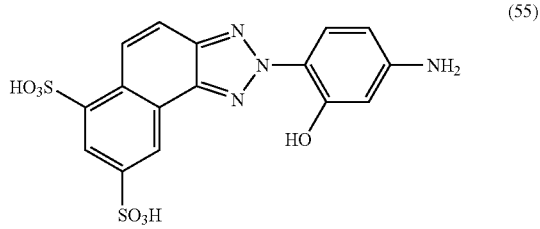

(55)

Except that the compound represented by the formula (47) was changed to the compound represented by the formula (55), 22.1 parts of a monoazo compound represented by the following formula (56) was obtained in the same manner as in Example 12.

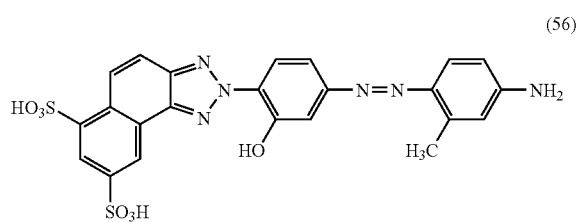

(56)

22.1 parts of the monoazo compound represented by the formula (56) was diazotized in the same manner as in Example 2. To the reaction mixture, 5.0 parts of 2,5-dimethylaniline dissolved in dilute aqueous hydrochloric acid was added and, while stirring at 30 to 40° C., the pH was adjusted to 3 by addition of sodium carbonate. By further stirring, the coupling reaction was completed to obtain 22 parts of a disazo compound represented by the following formula (57).

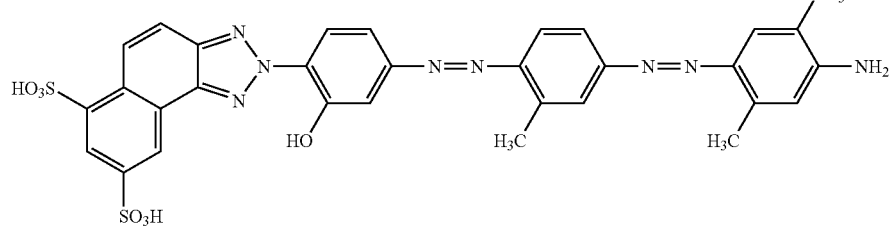

(57)

Except that the compound represented by the formula (49) was changed to the compound represented by the formula (57), 26 parts of the trisoazo compound represented by the formula (40) was obtained in the same manner as in Example 10. This compound was red-purple in color and its maximum absorption wavelength in a 20% pyridine-water solution was 570 nm.

Example 15

In an aqueous solution kept at 45° C. containing a dye, the compound (7) obtained in Example 1, in a concentration of 0.03% and sodium sulfate in a concentration of 0.1%, a polyvinyl alcohol film of 75 μm in thickness (trade name: VF-XS #7500, produced by Kuraray Co., Ltd.) was dipped for 4 minutes. This film was stretched 5 times at 50° C. in a 3% aqueous boric acid solution, and washed with water and dried in the stretched state to obtain a polarizing film.

The polarizing film obtained showed (a) the maximum absorption wavelength at 536 nm and (b) a polarization coefficient of 99.9%, thus having high polarization performance. The test methods are described in the following.

(a) Measurement of Maximum Absorption Wavelength (λmax) of the Polarizing Film

The maximum absorption wavelength was measured by use of a spectrophotometer (U-4100, produced by Hitachi Ltd.) in a state where two polarizing films were superimposed on each other in such a way that their orientation directions were perpendicular to each other (the perpendicular position).

(b) Measurement of Polarization Coefficient

Using the aforementioned spectrophotometer, light transmittance (Tp) in a state where the two polarizing films are superimposed parallel to each other (the parallel position) and light transmittance (Tc) in the perpendicular position were measured. The polarization coefficient was calculated according to the formula: polarization coefficient=$[(Tp-Tc)/(Tp+Tc)]^{1/2} \times 100(\%)$.

Example 16

Using the azo compounds described in Examples 2 to 14, just like the compound (7) above, polarizing films were obtained in the same manner as in Example 15. The maximum absorption wavelengths and polarizing coefficients of the polarizing films obtained are shown in Table 1.

TABLE 1

| Salt of azo compound | Maximum absorption wavelength (nm) | Polarization coefficient (%) |
|---|---|---|
| Compound of the formula (7) | 536 | 99.9 |
| Compound of the formula (9) | 575 | 99.9 |
| Compound of the formula (10) | 583 | 99.9 |
| Compound of the formula (12) | 575 | 99.9 |
| Compound of the formula (13) | 577 | 99.9 |
| Compound of the formula (14) | 547 | 99.9 |
| Compound of the formula (18) | 598 | 99.9 |
| Compound of the formula (19) | 623 | 99.9 |
| Compound of the formula (30) | 584 | 99.9 |
| Compound of the formula (33) | 575 | 99.9 |
| Compound of the formula (34) | 580 | 99.9 |
| Compound of the formula (36) | 585 | 99.9 |
| Compound of the formula (39) | 669 | 99.9 |
| Compound of the formula (40) | 578 | 99.9 |

Example 17

In an aqueous solution kept at 45° C. containing a dye, the compound (7) obtained in Example 1, in a concentration of 0.1% and a compound represented by the following structure (58) in a concentration of 0.01%, which is described in

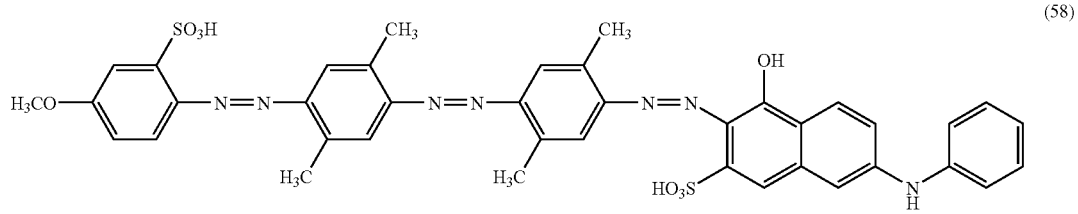

(58)

Example 1 of the Patent Document 6, a polyvinyl alcohol film of 75 μm in thickness was dipped for 4 minutes. This film was stretched 5 times at 50° C. in a 3% aqueous boric acid solution, and washed with water and dried in the stretched state to obtain a polarizing film. The polarizing film obtained showed the maximum absorption wavelength (λmax) at 552 nm, the single plate average light transmittance in a range of 500 to 580 nm of 42%, and average light transmittance at a perpendicular position of 0.01% or less, thus having a high degree of polarization. A dye-containing polarizing plate of the present invention was obtained by adhering a TAC film (80 μm in film thickness; trade name, TD-80U; produced by Fujifilm Corporation) on one surface of the polarizing film obtained and a film on another surface using a PVA adhesive, the film obtained by forming a UV (ultra violet) curable hard coat layer in a thickness of about 10 μm on one side of the TAC film. On one side of this polarizing plate, an acrylic ester pressure-sensitive adhesive was provided to afford an adhesive layer-carrying polarizing plate. Further, on the outside of the hard coat layer, an anti-reflection (AR) multi-coating was provided by a vacuum deposition method. This was cut in a size of 30 mm×40 mm and was adhered onto a glass plate of the same size having a transparent AR layer on one side. Thus, a color polarizing plate (for the green channel) with an AR support for a liquid crystal projector of the present invention was obtained. The color polarizing plate for a liquid crystal projector of the present Example had a high polarization coefficient and showed a long-term durability even under conditions of high temperature and high humidity. Also, resistance to prolonged exposure of light was excellent.

Example 18

In an aqueous solution kept at 45° C. containing of a dye, the compound (9) obtained in Example 2, in a concentration of 0.1% and a compound represented by the following structure (59), which is described in Example of Patent Document 2, in a concentration of 0.05%, a polyvinyl alcohol film of 75 μm in thickness was dipped for 4 minutes. This film was stretched 5 times at 50° C. in a 3% aqueous boric acid solution, washed with water and dried in the stretched state to obtain a polarizing film. The polarizing film obtained showed the maximum absorption wavelength (λmax) at 610 nm, a single plate average light transmittance in a range of 600 to 640 nm of 42%, and the average light transmittance at the perpendicular position of 0.01% or less, thus indicating a high degree of polarization. Using this polarizing film, a color polarizing plate (for the red channel) with an AR support for a liquid crystal projector of the present invention was obtained by the same process as in Example 17. The polarizing plate of the present Example had a high polarization coefficient and showed a long-term durability even under conditions of high temperature and high humidity. Also, resistance to prolonged exposure of light was excellent.

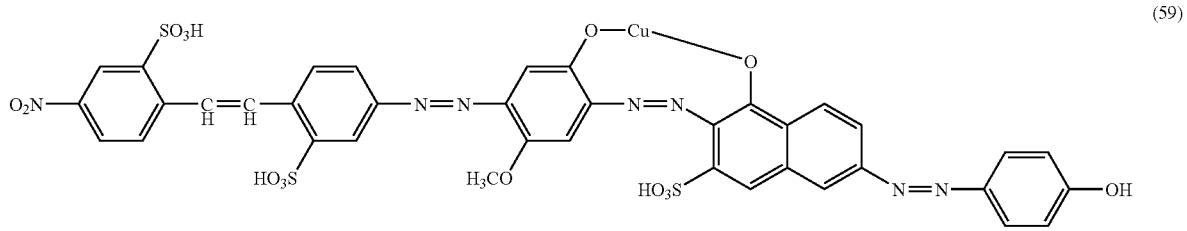

(59)

INDUSTRIAL APPLICABILITY

A polarizing plate, obtained by using a polarizing film containing an azo compound or a salt thereof of the present invention, has high polarization performance comparable to a polarizing plate using iodine, and also has excellent durability. Thus, the polarizing plate is suitable for various liquid crystal displays, liquid crystal projectors, in-vehicle application where high polarization performance and durability are required, and display applications for industrial measurement instruments used in various environments.

The invention claimed is:
1. An azo compound represented by the following formula (1) or a salt thereof:

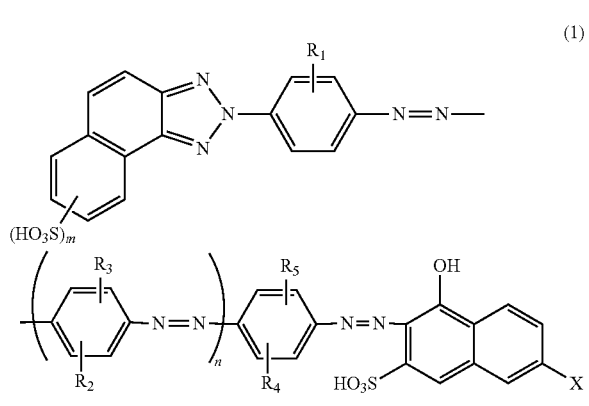

(1)

wherein $R_1$ represents a hydrogen atom, a lower alkyl group, a lower alkoxyl group, a hydroxyl group, a sulfonic acid group, or a carboxyl group; $R_2$ to $R_5$ each independently represent a hydrogen atom, a lower alkyl group, a lower alkoxyl group, or an acetylamino group; X represents a benzoylamino group which may have one or more substituents, a phenylamino group which may have one or more substituents, a phenylazo group which may have one or more substituents, or a naphthotriazole group which may have one or more substituents; m represents 1 or 2; and n represents 0 or 1.

2. An azo compound represented by the following formula (2) or a salt thereof:

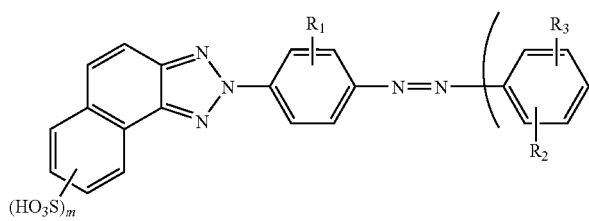

(2)

wherein $R_1$ represents a hydrogen atom, a lower alkyl group, a lower alkoxyl group, a hydroxyl group, a sulfonic acid group, or a carboxyl group; $R_2$ to $R_4$ each independently represent a hydrogen atom, a lower alkyl group, a lower alkoxyl group, or an acetylamino group; X represents a benzoylamino group which may have one or more substituents, a phenylamino group which may have one or more substituents, a phenylazo group which may have one or more substituents, or a naphthotriazole group which may have one or more substituents; m represents 1 or 2; and n represents 0 or 1.

3. The azo compound according to claim 1 or 2 or a salt thereof, wherein X is a benzoylamino group which may have one or more substituents, a phenylamino group which may have one or more substituents, a phenylazo group which may have one or more substituents, or a naphthotriazole group which may have one or more substituents, wherein each of the one or more substituents is independently a hydrogen atom, a lower alkyl group, a lower alkoxyl group, a hydroxyl group, a carboxyl group, a sulfonic acid group, a nitro group, an amino group, or a substituted amino group.

4. The azo compound according to claim 1 or 2 or a salt thereof, wherein X is a naphthotriazole group represented by the following formula (3):

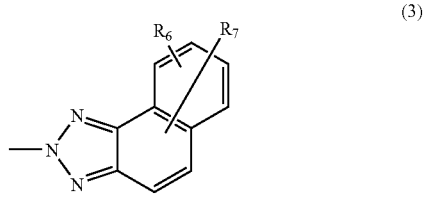

(3)

wherein $R_6$ and $R_7$ each independently represent either a hydrogen atom or a sulfonic acid group.

5. The azo compound according to claim 1 or 2 or a salt thereof, wherein X is a benzoylamino group represented by the following formula (4):

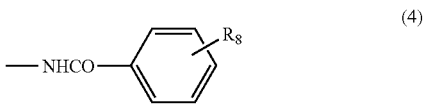

(4)

wherein $R_8$ represents either a hydrogen atom, an amino group, or a substituted amino group.

6. The azo compound according to claim 1 or 2 or a salt thereof, wherein X is a phenylamino group represented by the following formula (5):

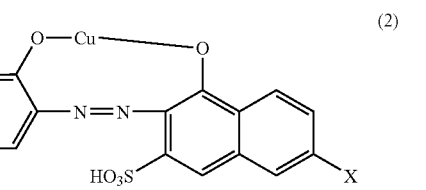

(5)

wherein $R_9$ and $R_{10}$ each independently represent any one of a hydrogen atom, a methyl group, a methoxy group, a sulfonic acid group, an amino group, or a substituted amino group.

7. The azo compound according to claim 1 or 2 or a salt thereof, wherein X is a phenylazo group represented by the following formula (6):

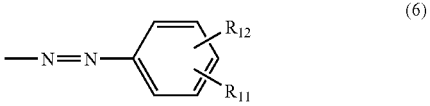

(6)

wherein $R_{11}$ and $R_{12}$ each independently represent any one of a hydrogen atom, a methyl group, a methoxy group, an amino group, a substituted amino group, or a hydroxyl group.

8. The azo compound according to claim 1 or a salt thereof, wherein $R_1$ is a hydrogen atom, a methyl group, a hydroxyl group, a carboxyl group, or a sulfonic acid group.

9. The azo compound according to claim 1 or a salt thereof, wherein each of $R_2$ to $R_5$ is independently a hydrogen atom, a methyl group, or a methoxy group.

10. A dye-containing polarizing film, comprising an azo compound according to claim 1 and/or a salt thereof, contained in a polarizing film substrate.

11. A dye-containing polarizing film, comprising an azo compound according to claim 1 and/or a salt thereof, and at least one kind of other organic dye, contained in a polarizing film substrate.

12. A dye-containing polarizing film, comprising at least two kinds of azo compounds according to claim 1 and/or salts thereof, and at least one kind of other organic dye, contained in a polarizing film substrate.

13. The azo compound according to claim 2 or a salt thereof, wherein $R_1$ is a hydrogen atom, a methyl group, a hydroxyl group, a carboxyl group, or a sulfonic acid group.

14. The azo compound according to claim 2 or a salt thereof, wherein each of $R_2$ to $R_5$ is independently a hydrogen atom, a methyl group, or a methoxy group.

15. A dye-containing polarizing film, comprising an azo compound according to claim 2 and/or a salt thereof, contained in a polarizing film substrate.

16. A dye-containing polarizing film, comprising an azo compound according to claim 2 and/or a salt thereof, and at least one kind of other organic dye, contained in a polarizing film substrate.

17. A dye-containing polarizing film, comprising at least two kinds of azo compounds according to claim 2 and/or salts thereof, and at least one kind of other organic dye, contained in a polarizing film substrate.

18. The dye-containing polarizing film according to any one of claims 10, 11, 12, 15, 16 and 17, wherein the polarizing film substrate is a film comprising a polyvinyl alcohol resin.

19. A dye-containing polarizing plate, comprising a transparent protective layer adhered on at least one side of a dye-containing polarizing film according to any one of claims 10, 11, 12, 15, 16 and 17.

20. A polarizing plate for a liquid crystal display, comprising a dye-containing polarizing film according to any one of claims 10, 11, 12, 15, 16 and 17.

21. A color polarizing plate for crystal projector, comprising a dye-containing polarizing film according to any one of claims 10, 11, 12, 15, 16 and 17.

22. A polarizing plate for a liquid crystal display, comprising a dye-containing polarizing film according to claim 18.

23. A polarizing plate for a liquid crystal display, comprising a dye-containing polarizing plate according to claim 19.

24. A color polarizing plate for a liquid crystal projector, comprising a dye-containing polarizing film according to claim 18.

25. A color polarizing plate for a liquid crystal projector, comprising a dye-containing polarizing plate according to claim 19.

* * * * *